(12) United States Patent
Zaghouani

(10) Patent No.: US 11,338,036 B2
(45) Date of Patent: May 24, 2022

(54) METHODS AND COMPOSITIONS FOR THE TREATMENT AND/OR PREVENTION OF TYPE 1 DIABETES

(71) Applicant: The Curators of the University of Missouri, Columbia, MO (US)

(72) Inventor: Habib Zaghouani, Columbia, MO (US)

(73) Assignee: The Curators of the University of Missouri, Columbia, MO (US)

(*) Notice: Subject to any disclaimer, the term of this patent is extended or adjusted under 35 U.S.C. 154(b) by 561 days.

(21) Appl. No.: 14/773,497

(22) PCT Filed: Mar. 10, 2014

(86) PCT No.: PCT/US2014/022321
§ 371 (c)(1),
(2) Date: Sep. 8, 2015

(87) PCT Pub. No.: WO2014/138725
PCT Pub. Date: Sep. 12, 2014

(65) Prior Publication Data
US 2016/0015811 A1    Jan. 21, 2016

Related U.S. Application Data

(60) Provisional application No. 61/775,115, filed on Mar. 8, 2013.

(51) Int. Cl.
| | | |
|---|---|---|
| *A61K 39/00* | (2006.01) |
| *A61K 39/395* | (2006.01) |
| *A61K 38/17* | (2006.01) |
| *C07K 16/18* | (2006.01) |
| *A61K 35/545* | (2015.01) |
| *A61K 38/10* | (2006.01) |
| *A61K 35/28* | (2015.01) |
| *A61K 38/51* | (2006.01) |

(52) U.S. Cl.
CPC ........ *A61K 39/39533* (2013.01); *A61K 35/28* (2013.01); *A61K 35/545* (2013.01); *A61K 38/10* (2013.01); *A61K 38/1774* (2013.01); *A61K 38/51* (2013.01); *C07K 16/18* (2013.01); *A61K 2039/505* (2013.01); *C07K 2318/10* (2013.01)

(58) Field of Classification Search
None
See application file for complete search history.

(56) References Cited

U.S. PATENT DOCUMENTS

| | | | |
|---|---|---|---|
| 3,773,919 | A | 11/1979 | Boswell et al. |
| 4,481,946 | A | 11/1984 | Altshuler et al. |
| 4,486,188 | A | 12/1984 | Altshuler et al. |
| 6,372,716 | B1 | 4/2002 | Bush et al. |
| 6,566,329 | B1 | 5/2003 | Meyn et al. |
| 6,685,940 | B2 | 2/2004 | Andya |
| 7,744,876 | B2 | 6/2010 | Zaghouani et al. |
| 2004/0126374 | A1 | 7/2004 | Zaghouani et al. |
| 2006/0115478 | A1 | 6/2006 | Zaghouani et al. |
| 2007/0041973 | A1 | 2/2007 | Zaghouani et al. |
| 2008/0241106 | A1 | 10/2008 | Austen et al. |
| 2012/0058105 | A1 | 3/2012 | NG et al. |

FOREIGN PATENT DOCUMENTS

| | | |
|---|---|---|
| WO | WO 93/15722 | 8/1993 |
| WO | WO 2005/026335 | 3/2005 |

OTHER PUBLICATIONS

Zhang, C., et al. Proc. Nat'l. Acad. Sci. 2007;104(7):2337-2342.*
Kang, S., et al. Diabetes 2012;61:866-876.*
Loomans et al. Diabetes, 2004;53:195-199.*
Aguayo-Mazzucato et al., "Stem cell therapy for type 1 diabetes mellitus," Nature Reviews 6(3):139-148 (Mar. 1, 2010).
Bach, "Insulin-dependent diabetes mellitus as an autoimmune disease," Endroc. Rev. 15(4):516-542 (Aug. 1994) (Abstract only).
Brissova et al., "Pancreatic islet production of vascular endothelial growth factor-a is essential for islet vascularization, revascularization, and function," Diabetes, 55(11):2974-85 (Nov. 2006).
Brumeanu et al., "Efficient loading of identical viral peptide onto class II molecules by antigenized immunoglobulin and influenza virus," J. Exp. Med. 178(5):1795-9 (Nov. 1, 1993).
Castano et al., "Type-I diabetes: a chronic autoimmune disease of human, mouse, and rat," Ann. Rev. Immunol. 8:647-680 (1990).
Choi et al., Little evidence of transdifferentiation of bone marrow-derived cells into pancreatic beta cells, Diabetologia, 46:1366-1374 (2003).
Couri et al., "C-peptide levels 1-12 and insulin independence following autologous nonmyeloablative hematopoietic stem cell transplantation in newly diagnosed type 1 diabetes mellitus," The Journal of the American Medical Association 301(15):1573-1579 (Apr. 15, 2009).
Eggermann et al., "Endothelial progenitor cell culture and differentiation in vitro: a methodological comparison using human umbilical cord blood," Cardiovascular Research 58(2):478-86 (May 1, 2003).
Eppstein et al., "Biological activity of liposome-encapsulated murine interferon gamma is mediated by a cell membrane receptor," Proc. Natl. Acad. Sci. USA, 82(11):3688-92 (Jun. 1985).
Freeborn et al., "Identifying challenges of living with type 1 diabetes: child and youth perspectives," J. Clin. Nurs. 22:1890-98 (2013).
Gregg et al., "A sudden decline in active membrane-bound TGF-beta impairs both T regulatory cell function and protection against autoimmune diabetes," J. Immunol., 173(12):7308-16 (Dec. 15, 2004) (Abstract only).
Gregg et al., "IL-10 diminishes CTLA-4 expression on islet-resident T cells and sustains their activation rather than tolerance," J. Immunol., 174:662-70 (Jan. 15, 2005) (Abstract only).

(Continued)

*Primary Examiner* — G. R. Ewoldt
(74) *Attorney, Agent, or Firm* — Perkins Coie LLP

(57) ABSTRACT

The disclosure relates generally to methods and compositions of treating or preventing diabetes mellitus by administering to a subject a composition comprising an amount of stem and/or progenitor cells and at least one antigen-specific therapy.

13 Claims, 10 Drawing Sheets
Specification includes a Sequence Listing.

(56) References Cited

OTHER PUBLICATIONS

Hess et al., "Bone marrow-derived stem cells initiate pancreatic regeneration," Nat. Biotechnol., 21(7):763-70 (Jul. 2003) (Abstract only).

Jain et al., "Innocuous IFN γ induced by adjuvant-free antigen restores normoglycemia in NOD mice through inhibition of IL-17 production," J. Exp. Med., 205(1):207-18 (Jan. 21, 2008).

Lammert et al., "Role of VEGF-A in vascularization of pancreatic islets," Curr. Biol., 13(12):1070-74 (Jun. 17, 2003).

Langer et al., "Biocompatibility of polymeric delivery systems for macromolecules," J. Biomed. Mater. Res., 15:167-277 (1981) (Abstract only).

Lechner et al., "No evidence for significant transdifferentiation of bone marrow into pancreatic beta-cells in vivo," Diabetes, 53(3):616-23 (Mar. 2004).

Legge et al., "Coupling of peripheral tolerance to endogenous interleukin 10 promotes effective modulation of myelin-activated T cells and ameliorates experimental allergic encephalomyelitis," J. Exp. Med., 191(12):2039-52 (Jun. 19, 2000).

Legge et al., "On the role of dendritic cells in peripheral T cell tolerance and modulation of autoimmunity," J. Exp. Med., 196(2):217-27 (2002).

Legge et al., "Presentation of a T cell receptor antagonist peptide by immunoglobulins ablates activation of T cells by a synthetic peptide or proteins requiring endocytic processing," J. Exp. Med. 185(6):1043-54 (Mar. 17, 1997).

Li et al., "Functional characterization and expression profiling of human induced pluripotent stem cell- and embryonic stem cell-derived endothelial cells," Stem Cells and Development. 20:1701-10 (Oct. 2011).

Livingstone et al., "Risk of cardiovascular disease and total mortality in adults with type 1 diabetes: Scottish registry linkage study," PLoS Med. 9(10):e1001321 (2012).

Mathews et al., "Recruitment of bone marrow-derived endothelial cells to sites of pancreatic beta-cell injury," Diabetes, 53(1):91-8 (Jan. 2004).

Miller et al., "Antigen-specific tolerance strategies for the prevention and treatment of autoimmune disease," Nat. Rev. Immunol. 7(9):665-77 (Sep. 2007) (Abstract only).

Miltenyi et al., "High gradient magnetic cell separation with MACS," Cytometry. 11(2):231-238 (1990) (Abstract only).

Secrest et al., "All-cause mortality trends in a large population-based cohort with long-standing childhood-onset type 1 diabetes: the Allegheny County type 1 diabetes registry," Diabetes Care. 33(12):2573-79 (Dec. 2010).

Sidman et al., "Controlled release of macromolecules and pharmaceuticals from synthetic polypeptides based on glutamic acid," Biopolymers, 22(1):547-556 (Jan. 1983) (Abstract only).

Simone et al., "Immunologic "vaccination" for the prevention of autoimmune diabetes (type 1A)," Diabetes Care. 22 (Suppl. 2):B7-B15 (1999) (Abstract only).

Tisch et al., "Insulin-dependent diabetes mellitus," Cell. 85(3):291-7 (May 1996).

Van Belle et al., "Type 1 diabetes: etiology, immunology, and therapeutic strategies," Physiol. Rev. 91(1):79-118 (Jan. 2011).

Wallet et al., "MerTK regulates thymic selection of autoreactive T cells," Proc. Natl. Acad. Sci. 106(12):24810-5 (Mar. 24, 2009).

Zaghouani et al., "Presentation of a viral T cell epitope expressed in the CDR3 region of a self immunoglobulin molecule," Science. 259:224-7 (Jan. 8, 1993) (Abstract only).

\* cited by examiner

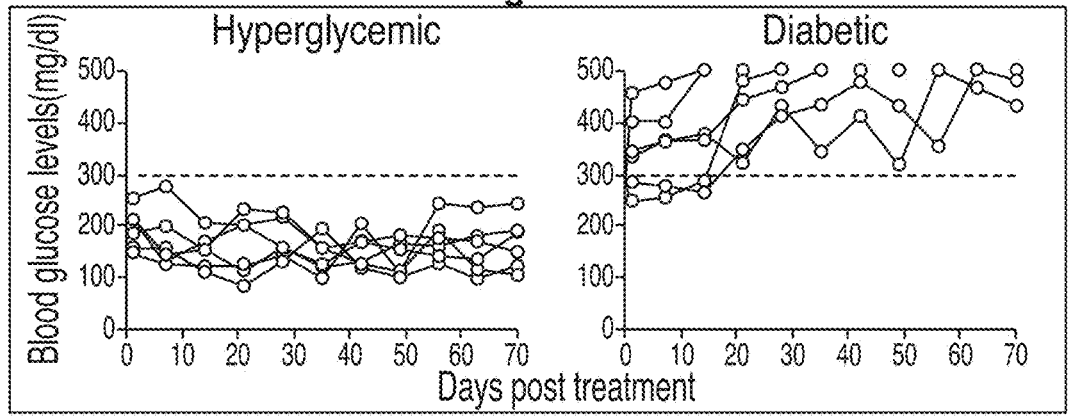
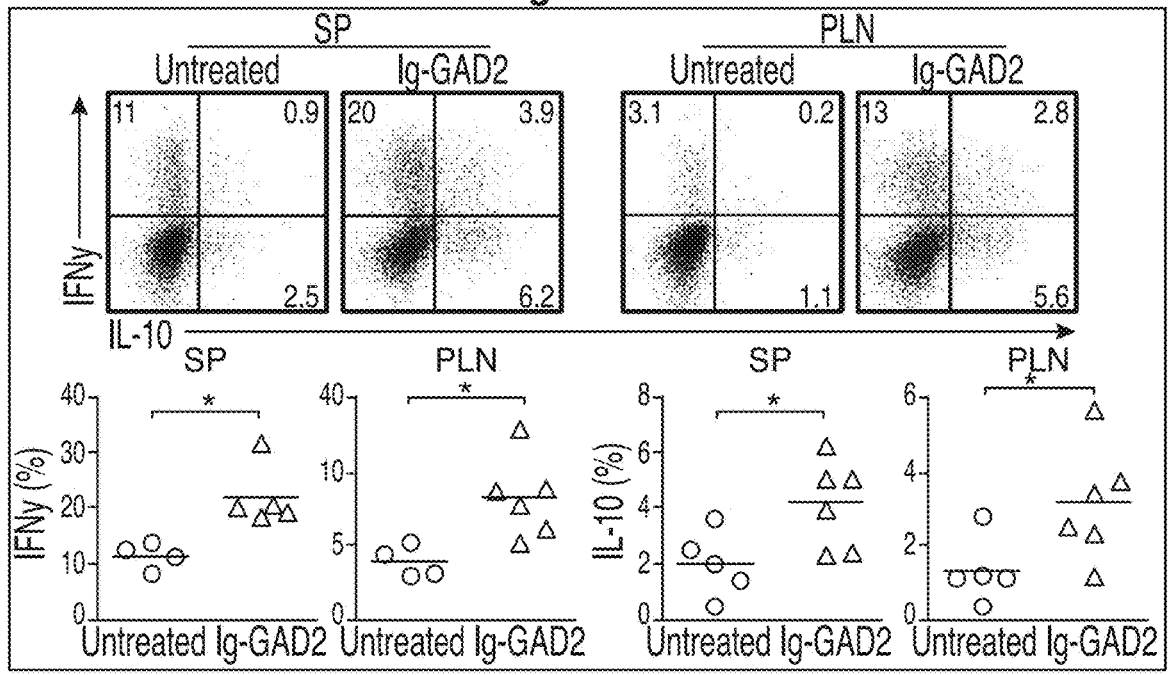
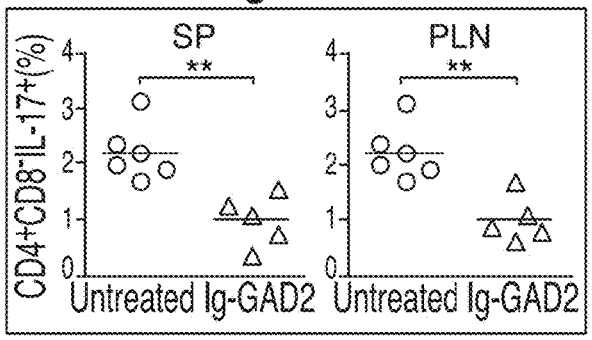
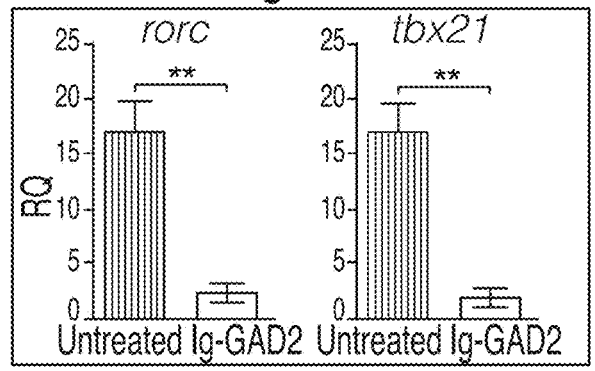

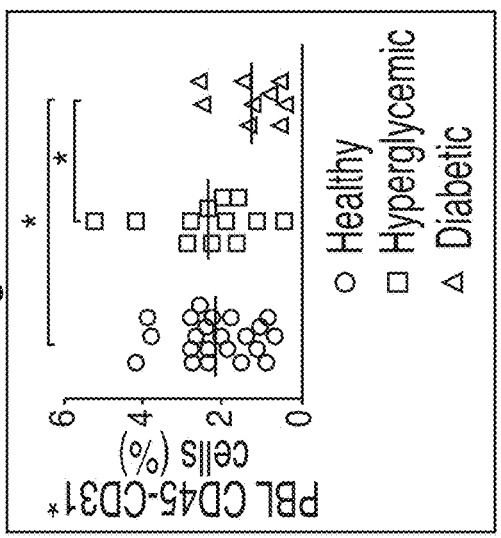
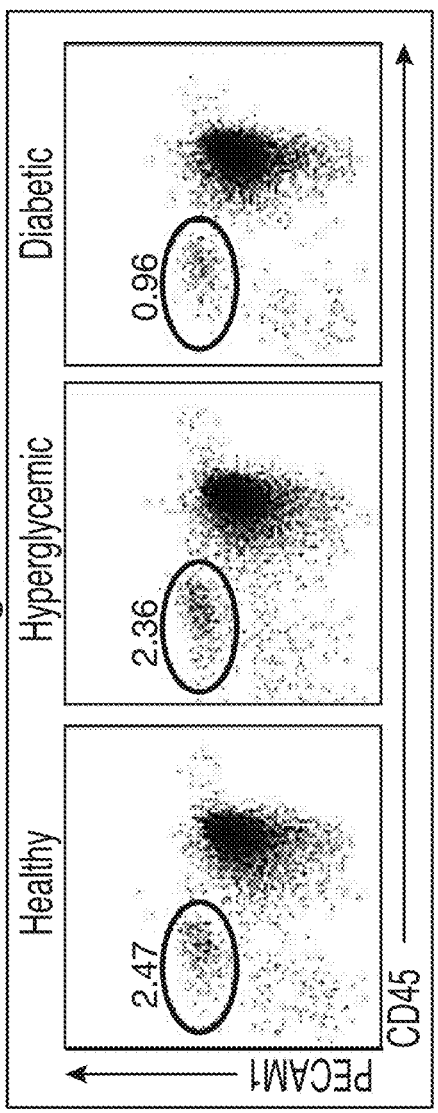
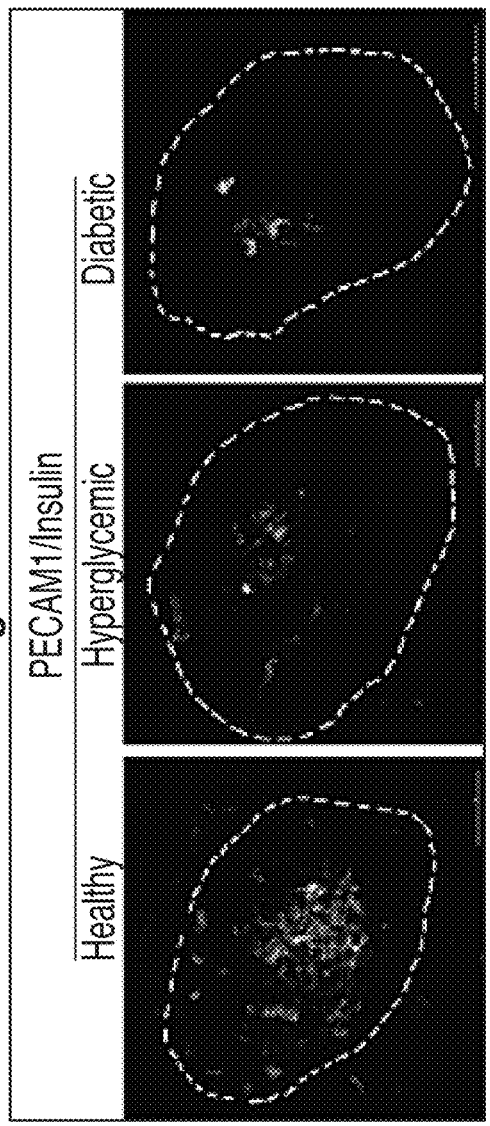

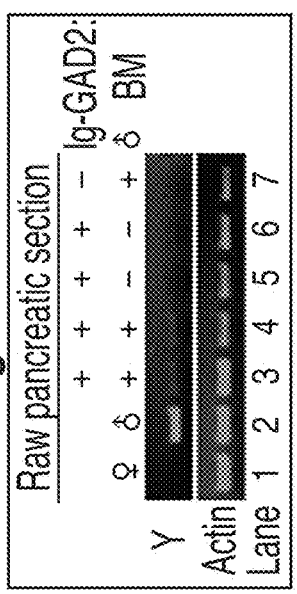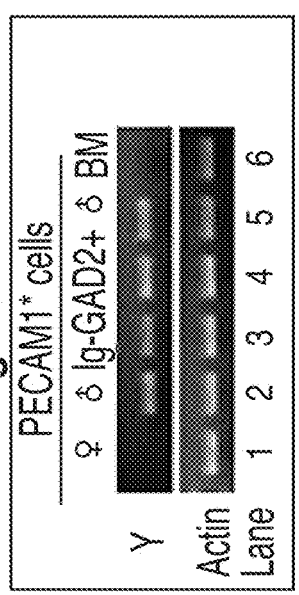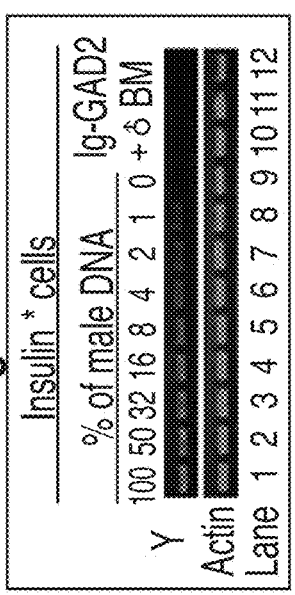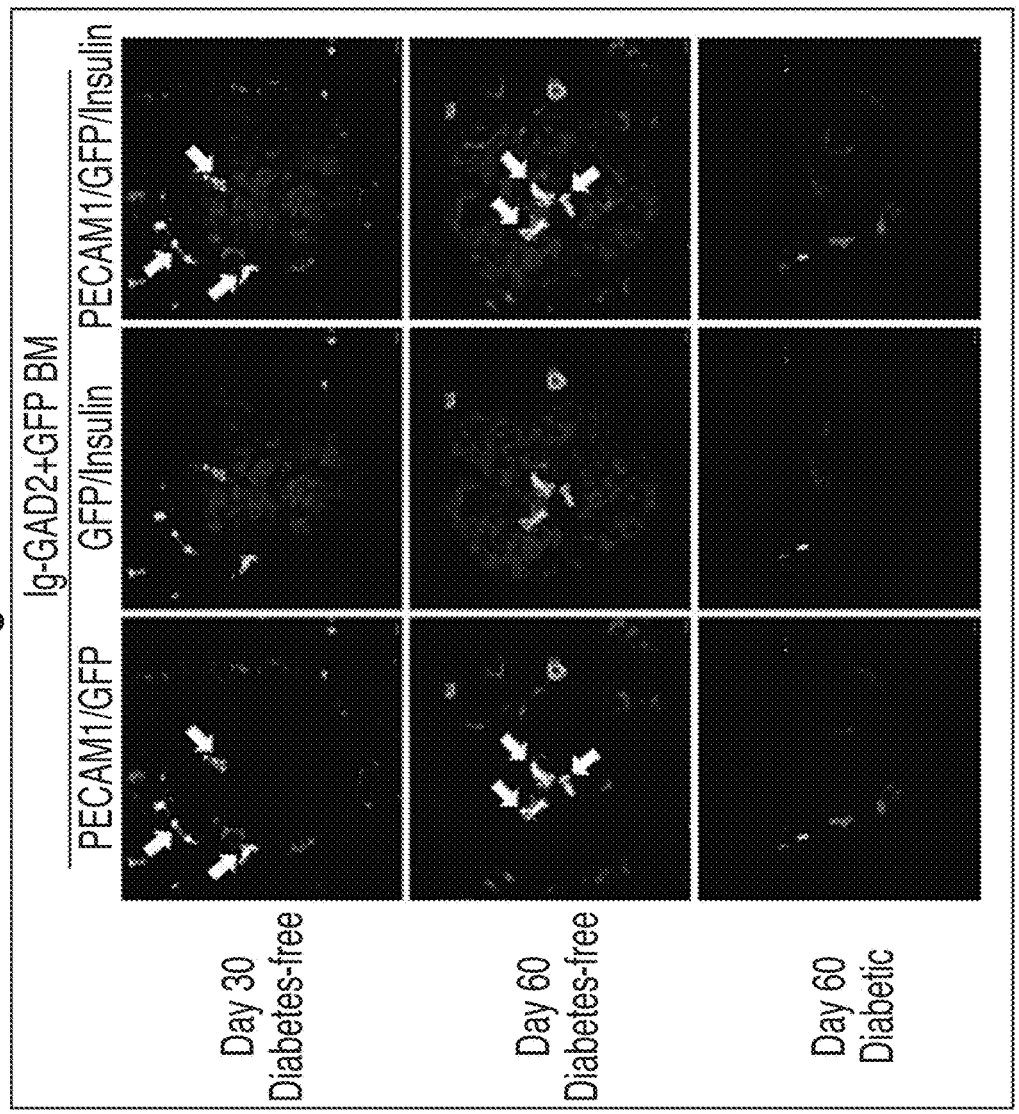

METHODS AND COMPOSITIONS FOR THE TREATMENT AND/OR PREVENTION OF TYPE 1 DIABETES

PRIORITY CLAIM

This application is a 35 USC § 371 U.S. National Stage Application of International Patent Application No. PCT/US2014/022321, filed Mar. 10, 2014, entitled "Methods and Compositions for the Treatment and/or Prevention of Type 1 Diabetes," which claims priority to U.S. provisional patent application Ser. No. 61/775,115 filed Mar. 8, 2013, the entire contents of which are incorporated herein by reference and relied upon.

STATEMENT REGARDING FEDERALLY SPONSORED RESEARCH

This work was supported by grant number R56-AI-095235 from the United States Government funded through the National Institutes of Health. The U.S. Government has certain rights in this invention.

SEQUENCE LISTING

This application includes a Sequence Listing, which was submitted in ASCII format via EFS-Web and is hereby incorporated by reference in its entirety. The ASCII text file, created on Mar. 8, 2013, is named "Sequence Listing" and is 3 kilobytes in size.

FIELD

The present invention relates generally to methods and compositions for treating or preventing type 1 diabetes ("T1D").

BACKGROUND

Type 1 diabetes (T1D), once known as juvenile diabetes, is an autoimmune-mediated disease that specifically targets the pancreatic beta cells (Castano et al., *Ann. Rev. Immunol.* 8:647-680 (1990)). Disease pathogenesis involves T cell infiltration into the islets of the pancreas, which results in the subsequent destruction of the insulin producing beta cells (Bach, *Endroc. Rev.* 15:516-542 (1994)). Without insulin, blood sugar (glucose) is unable to be stored and later used for energy (Bach, *Endroc. Rev.* 15:516-542 (1994)). Early symptoms of T1D include frequent urination, extreme fatigue and irritability (Van Belle et al., *Physiol. Rev.* 91:79-118 (2011)). Prolonged exposure to high levels of glucose in the bloodstream can cause serious damage to organ systems throughout the body (Bach, *Endroc. Rev.* 15:516-542 (1994)). The exact cause of T1D is unknown, but autoimmune, genetic and environmental factors are suspected (Tisch et al., *Cell.* 85:291-297 (1996)). Roughly three million people world-wide, one million being Americans, suffer from T1D with a reported increase in the rate of increase ranging from 3 to 5 percent a year (Melmed et al., Williams Textbook of Endocrinology: 12th Edition (2011)). Despite the high incidence of disease there remains no cure for diabetes. People afflicted with T1D must resort to diet modifications, constant monitoring of their blood glucose level and either insulin injections or continuous insulin infusion through a pump (Freeborn et al., *J. Clin. Nurs.* doi: 10.1111/jocn.120462013)). Mismanagement of blood glucose levels, for even a short period of time, can result in serious consequences including: kidney failure, vision changes, heart disease, stoke or even death (Simone et al., *Diabetes Care.* 22 (Suppl. 2): B7-B15 (1999); Livingstone et al., *PLoS Med.* 9(10): e1001321 (2012); Secrest et al., *Diabetes Care.* 33:2573-2579 (2010)).

As with many autoimmune diseases, T1D likely involves multiple autoantigens and diverse T cell specificities (Bach, *Endroc. Rev.* 15:516-542 (1994); Tisch et al., *Cell.* 85:291-297 (1996)). Immunoglobulins ("Igs") genetically modified to express self and altered self peptides (Ig-chimeras) can be used to suppress pathological immune responses (Miller et al., *Nat. Rev. Immunol.* 7:665-677 (2007)). These Ig-chimeras have been shown to increase presentation to T cells by 100-fold relative to free peptide due to the internalizing of the Ig-chimera, processing within the endosomal compartment and unlimited access of the peptides to newly synthesized MHC molecules (Zaghouani et al., *Science.* 259:224-227 (1993); Legge et al., *J. Exp. Med.* 185:1043-1053 (1997); Brumeanu et al., *J. Exp. Med.* 178:1795-1799 (1993)). Since Igs are self-molecules, side effects are minimal even when repetitive injections are required and are thus conducive to continuous therapy. Ig-chimeras allow for the specific blockade of the harmful effects of self-reactive immune cells, while maintaining the ability of the body's immune system to clear foreign antigens (Miller et al., *Nat. Rev. Immunol.* 7:665-677 (2007)). Therefore, Ig-chimeras, expressing diabetogenic peptides, are attractive antigen-specific therapeutic approaches to treat or prevent T1D.

SUMMARY

The present disclosure provides methods and compositions for treating or preventing type 1 diabetes ("T1D in a subject in need thereof. In one aspect, the present disclosure provide methods for the delivery of an antigen-specific therapy for the down regulation of diabetogenic T cells (immune modulation) and the concurrent administration of stem and/or progenitor cells for the regeneration of endothelial cells in the pancreatic islets for the treatment or prevention of T1D.

The present disclosure provides methods of treating or preventing diabetes mellitus in a subject in need thereof, the method comprising: administering to the subject a composition comprising an amount of one or more stem and/or progenitor cells and an amount of at least one antigen-specific therapy, in a therapeutically effective amount.

The present disclosure also provides compositions comprising an amount of one or more stem and/or progenitor cells and an amount of at least one antigen-specific therapy, in a therapeutically effective amount.

The present disclosure also provides compositions comprising an amount of one or more stem and/or progenitor cells and an amount of at least one antigen-specific therapy in a therapeutically effective amount to sustain β-cell and endothelial cell formation and reverse diabetes mellitus.

The present disclosure also provides methods of treating or preventing diabetes mellitus in a subject in need thereof, the method comprising: administering to the subject a composition comprising an amount of purified bone marrow endothelial progenitor cells and an immunoglublin Ig-GAD2, in a therapeutically effective amount.

In an embodiment of any of the above-described methods or compositions, the diabetes mellitus is type 1 diabetes.

In an embodiment of any of the above-described methods or compositions, the subject is a mammal including, for example, a human.

In an embodiment of any of the above-described methods or compositions, the stem and/or progenitor cells are totipotent, pluripotent, multipotent or unipotent.

In an embodiment of any of the above-described methods or compositions, the stem and/or progenitor cells are isolated from bone marrow.

In an embodiment of any of the above-described methods or compositions, the stem and/or progenitor cells are purified bone marrow endothelial progenitor cells.

In an embodiment of any of the above-described methods or compositions, the stem and/or progenitor cells are allogenic cells.

In an embodiment of any of the above-described methods or compositions, the stem and/or progenitor cells are autologous cells.

In an embodiment of any of the above-described methods or compositions, the at least one antigen-specific therapy is an immunoglobulin-polypeptide chimera.

In an embodiment of any of the above-described methods or compositions, the immunoglobulin-polypeptide chimera is soluble.

In an embodiment of any of the above-described methods or compositions, the immunoglobulin-polypeptide chimera is aggregated.

In an embodiment of any of the above-described methods or compositions, the immunoglobulin-polypeptide chimera comprises an immunoglobulin having a CDR3 region, and wherein a diabetogenic epitope is inserted within the CDR3 region.

In an embodiment of any of the above-described methods or compositions, the diabetogenic epitope is derived from GAD, for example comprises GAD2 (SEQ ID NO: 1) or GAD1 (SEQ ID NO: 2).

In an embodiment of any of the above-described methods or compositions, the diabetogenic epitope is derived from INSβ, for example, comprises INSβ. (SEQ ID NO: 3).

BRIEF DESCRIPTION OF THE FIGURES

The foregoing summary, as well as the following detailed description of the disclosure, will be better understood when read in conjunction with the appended figures. For the purpose of illustrating the disclosure, shown in the figures are embodiments which are presently preferred. It should be understood, however, that the disclosure is not limited to the precise arrangements, examples and instrumentalities shown.

FIG. 1A-D shows Ig-GAD2 treatment alone could not overcome overt T1D despite induction of immune tolerance. FIG. 1A shows no restoration of normoglycemia in overtly diabetic mice treated with Ig-GAD2. The lower panels indicate that, despite the inability of Ig-GAD2 to restore normoglycemia, the treatment resulted in an induction of immune tolerance as shown by an eradication of Th17 cells but retention of Th1 cells in the spleen and an increase in IFNγ and/or IL-10 in the Ig-GAD2 treated diabetic mice (FIG. 1B-D).

FIG. 2A depicts a schematic representation of the treatment regimen. FIG. 2B shows an increase in the percentage of mice sustaining normoglycemia after receiving a combination treatment of Ig-GAD2+BM as compared to mice receiving BM or Ig-GAD2 alone. FIG. 2C shows an increase in cytokine production in splenic and pancreatic cells of mice receiving Ig-GAD2+BM. FIG. 2D shows a decrease in IL-17 producing cells in both the spleen and pancreas. FIG. 2E shows a decrease in the signature transcription factors of Th1 and Th17 cells.

FIG. 3A-D shows sustained restoration of normoglycemia in mice recipient of the Ig-GAD2+BM treatment as compared to Ig-GAD2 or BM treatment alone. Mice recipient of the Ig-GAD2+BM treatment had more islets that were mostly free of insulitis with minimal infiltration and abundant insulin-positive cells and more β-cells (FIG. 3B-C. Moreover, treatment with the Ig-GAD2+BM restored the number of insulin producing cells and β-cell mass (FIG. 3E-G).

FIG. 4A-D shows the decline of PECAM1-expressing endothelial cells in both the peripheral blood and pancreas during the progression from healthy to hyperglycemic to diabetes.

FIG. 5A shows increased PECAM1 and insulin staining in pancreatic islet sections from mice treated with Ig-GAD2+BM as compared to those mice receiving Ig-GAD2 or BM alone. FIG. 5B shows the increase in functional markers for endothelial cells in mice receiving Ig-GAD2+BM relative to untreated diabetic mice. Pancreatic sections from Ig-GAD2+BM treated mice display and increased number of insulin$^+$ki-67$^+$ pancreatic cells (FIG. 5C).

FIG. 6A-D shows that the new pancreatic endothelial cells are derived from the donor BM.

FIG. 7A-B shows that BM cells expressing the endothelial progenitor cell (EPC) markers c-kit and FLK-1 were significantly reduced in diabetic versus age-matched healthy mice. Diabetic mice receiving EPCs from healthy donors exhibited a higher recovery rate as compared to whole BM-recipient mice (FIG. 7C). EPCs isolated from diabetic NOD-GFP mice resulted in minimal disease recovery and minimal engraftment of GFP cells into the pancreatic islets (FIG. 7C-D).

FIG. 10B shows newly formed insulin producing β-cells also produced VEGFa.

DETAILED DESCRIPTION

Figure 2A:
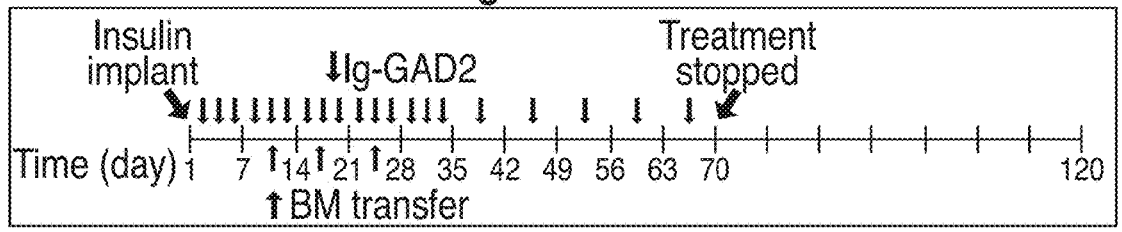
FIG. 2A-E shows the restoration of normoglycemia in overtly diabetic mice treated with the Ig-GAD2 and bone marrow (BM) transplantation.

Effective therapies for use in treating diabetes including, Type 1 diabetes (T1D), have remained an important medical need. An antigen-specific therapy (e.g., Ig-GAD) was recently found to induce immune modulation in hyperglycemic subjects that was able to control pancreatic inflammation, stimulate β-cell regeneration and prevent T1D progression. However, when the same antigen-specific therapy was given to subjects with overt T1D it was unable to reverse the course of disease, despite immune modulation similar to that seen in the treatment of hyperglycemic subjects. Surprisingly, the inventor has discovered that an antigen-specific therapy is capable of sustaining recovery from overt T1D when accompanied with transfer of bone marrow (BM) cells (e.g., progenitor cells). As such, the present disclosure provides compositions and methods for treating or preventing T1D. Such methods may include selecting a subject with T1D, and administering to the subject an effective amount of a composition comprising an amount (e.g., an effective amount) of one or more stem and/or progenitor cells and an amount (e.g., an effective amount) of at least one antigen-specific therapy. The disclosed compositions and methods may be used to replace or complement other pharmaceutical approaches used in the treatment and/or prevention of T1D.

The present disclosure provides methods of treating or preventing diabetes mellitus in a subject in need thereof, the method comprising: administering to the subject a composition comprising an amount of one or more stem and/or progenitor cells and an amount of at least one antigen-specific therapy, in a therapeutically effective amount.

The present disclosure also provides compositions comprising an amount of one or more stem and/or progenitor cells and an amount of at least one antigen-specific therapy, in a therapeutically effective amount.

The present disclosure also provides compositions comprising an amount of one or more stem and/or progenitor cells and an amount of at least one antigen-specific therapy in a therapeutically effective amount to sustain β-cell and endothelial cell formation and reverse diabetes mellitus.

In one embodiment of the present disclosure, the diabetes mellitus is type 1 diabetes. Type 1 diabetes (T1D) is characterized by an autoimmune attack on and loss of the insulin-producing beta cells (β-cells) of the islets of Langerhans in the pancreas. The disease progresses through several stages commonly referred to in the field as pre-insulitis, insulitis, hyperglycemia, and overt diabetes. Diagnosis of the disease stage may be determined by blood glucose level, degree of infiltration of lymphocytes into pancreatic cells, and pancreatic β-cell mass. As used herein, the term "insulitis" refers to the occurrence of pancreatic infiltration, such that the affected islets have lost most of their β-cell mass (about 80% loss). As used herein, the term "pre-insulitis" refers to earlier stages of pancreatic infiltration such that there is a lesser degree of β-cell mass loss (about a 0%-40% loss). As used herein, the term "hyperglycemia" refers to the occurrence of higher than normal fasting blood glucose levels, usually greater than about 126 mg/dL. As used herein, the term "overt diabetes" refers to a diagnosis of full-blown diabetes in a subject based on the plasma glucose levels, usually of about 300 mg/dL or greater, pancreatic infiltration, and high reduction in β-cell mass.

In one embodiment, the composition is administered to the subject in the preinsultis stage of T1D. In yet another embodiment, the composition is administered to the subject before the subject has undergone IAA seroconversion. In yet another embodiment, the composition is administered to the subject before the subject has seroconverted and produces autoantibodies against one or more β-cell associated antigens. In still another embodiment, the composition is administered to a subject that is IAA-positive. In another embodiment, the composition is administered to a subject in the insulitis stage of T1D. In yet another embodiment, the compound is administered to a subject before the subject has developed hyperglycemia. In another embodiment of the invention, the subject has developed hyperglycemia when treatment is initiated. In yet another embodiment, the subject has been diagnosed with overt diabetes.

In an embodiment of any of the above-described methods or compositions, the subject is a mammal including, for example, a human.

The terms "treatment", "treat" and "treating" as used with respect to methods as described herein refer to eliminating, reducing, suppressing or ameliorating, either temporarily or permanently, either partially or completely, a clinical symptom, manifestation or progression of T1D (e.g., diagnosed symptom, manifestation or progression of an event, disease or condition). In addition, or alternatively, the terms "treatment", "treat" and "treating" as used herein with respect to the methods as described refer to inhibiting, delaying, suppressing, reducing, treating, eliminating or ameliorating, either temporarily or permanently, either partially or completely, a clinical symptom or manifestation of T1D. In some embodiments the treating is effective to reduce a symptom, sign, and/or condition of T1D in a subject by at least about 10% (e.g., 15%, 20%, 25%, 30%, 35%, 40%, 45%, 50%, 55%, 60%, 65%, 70%, 75%, 80%, 85%, 90%, 95%, or 100%) including, as compared to a baseline measurement of the symptom, sign, and/or condition made prior to the treatment. In some embodiments, the treating is effective to improve an assessment used to diagnose T1D in a subject including, as compared to a baseline assessment made prior to the treatment. Such treating as provided herein need not be absolute to be useful.

The term "prevention," "prevent," or "preventing" as used herein refers to eliminating or reducing the incidence or onset of T1D as described herein, as compared to that which would occur in the absence of the measures taken.

The term "in need of treatment" as used herein refers to a judgment made by a caregiver that a patient requires or will benefit from treatment. This judgment is made based on a variety of factors that are in the realm of a caregiver's expertise, but that includes the knowledge that the patient exhibits a clinical symptom or manifestation of T1D.

The term "effective amount" as used herein refers to an amount of a composition (e.g., a composition comprising an amount of one or more stem and/or progenitor cells and an amount of at least one antigen-specific therapy), either alone or as a part of a pharmaceutical composition, that is capable of having any detectable, positive effect on any symptom, aspect, parameter or characteristics of a disease state or condition when administered to a subject (e.g., as one or more doses). Such effect need not be absolute to be beneficial.

Stem & Progenitor Cells and Antigen-Specific Therapy

Any stem and/or progenitor cell and antigen-specific therapy is contemplated by the present disclosure.

Stem and/or progenitor cells can be isolated from numerous tissues of the body. As used herein, the term "stem cell" refers to an undifferentiated cell that is capable of self-renewal, meaning that with each cell division at least one daughter cell will also be a stem cell. A stem cell is also capable of differentiating into a more mature cell type (e.g., cells of the ecto-, meso-, and/or endo-dermal cell lineages). As used herein, the term "progenitor cell" refers to an undifferentiated cell derived from a stem cell, capable of self-renewal and differentiation, but typically with a more limited developmental potential as compared to a stem cell.

In an embodiment, the stem and/or progenitor cells are totipotent, pluripotent, multipotent or unipotent. As used herein, the term "totipotent" means having unlimited capability to give rise to any cell type of the body and all extraembryonic cell types. As used herein, the term "pluripotent" means having unlimited capability to give rise to any cells of the body. As used herein, the term "multipotent" means having the unlimited capability to give rise to more than one, but not all, cell types of the body. As used herein, "unipotent" means having the capability to give rise to only one cell type.

As used herein, the term "isolated" with reference to a cell, refers to a cell that is in an environment different from that which the cell naturally occurs (e.g. where the cell naturally occurs in an organism) and the cell is removed from its natural environment. Stem cells can be isolated from embryonic, fetal, post-natal, juvenile or adult tissues. Stem cells can also be isolated by from a somatic cell and induced into a stem cell-like state through any means and methods known to artisans skilled field (e.g., viral-, RNA-, protein, miRNA-, chemical-mediated reprogramming methods). Progenitor cells are typically found in post-natal animals, residing in tissues and organs in need of cellular repair or replacement (e.g. satellite cells found in muscles, neural progenitors found in regions of the brain, endothelial progenitor cells found in bone marrow).

In an embodiment, the stem and/or progenitor cells are isolated from bone marrow (BM). BM samples may typically be obtained from iliac crest, femora, tibiae, spine, rib or other medullar spaces of a subject. Bone marrow cells can be easily isolated using methods know in the art. For example, bone marrow cells can be isolated by bone marrow aspiration. U.S. Pat. No. 4,481,946 describes a bone marrow aspiration method and apparatus, wherein efficient recovery of bone marrow from a donor can be achieved by inserting a pair of aspiration needles at the intended site of removal. Through connection with a pair of syringes, the pressure can be regulated to selectively remove bone marrow and sinusoidal blood through one of the aspiration needles, while positively forcing an intravenous solution through the other of the aspiration needles to replace the bone marrow removed from the site. The bone marrow and sinusoidal blood can be drawn into a chamber for mixing with another intravenous solution and thereafter forced into a collection bag.

U.S. Pat. No. 4,486,188 describes methods of bone marrow aspiration and an apparatus in which a series of lines are directed from a chamber section to a source of intravenous solution, an aspiration needle, a second source of intravenous solution and a suitable separating or collection source. The chamber section is capable of simultaneously applying negative pressure to the solution lines leading from the intravenous solution sources in order to prime the lines and to purge them of any air. The solution lines are then closed and a positive pressure applied to redirect the intravenous solution into the donor while negative pressure is applied to withdraw the bone marrow material into a chamber for admixture with the intravenous solution, following which a positive pressure is applied to transfer the mixture of the intravenous solution and bone marrow material into the separating or collection source.

In another embodiment, the stem and/or progenitor cells are isolated from peripheral blood. Methods of collecting peripheral blood are known in the art, and any known method can be used to collect peripheral blood.

In an embodiment, the stem and/or progenitor cells are purified bone marrow endothelial progenitor cells. Endothelial progenitor cells (EPCs) are purified by depleting whole bone marrow (BM) or peripheral blood of lineage+(Lin+) cells using a lineage cell depletion kit. The Lin$^-$ cells are then stained with anti-c-Kit, anti-FLK-1, or any other markers of EPCs known to those skilled in the field, such as CD34. Cells are also labeled with 7-amino-actinomycin D (7-AAD) to distinguish between live and dead cells. The c-Kit$^+$7-AAD$^-$Flk-1$^+$ population represent the purified live EPCs. Cell sorting may be performed by any method known in the art to sort cells. A preferred sorting procedure is by fluorescent activated cell sorting (FACS). Magnetic bead cell sorting (MACS) of endothelial progenitors is preferred. The conventional MACS procedure is described by Miltenyi et al., *Cytometry.* 11:231-238 (1990). An especially preferred sorting procedure is by label free sorting methods. EPCs can be isolated and purified using techniques that are well known to those of skill in the art.

The stem and/or progenitors provided herein may be expanded in vitro for a period of time before being administered to an individual using cell culture protocols that are known in the art. Methods employed for growing and expanding EPCs in vitro can, for example, be such as those described in Eggermann et al., *Cardiovascular Research.* 58:478-486 (2003). In some methods the cells may be differentiated in vitro into cells of the endothelial lineage using differentiation protocols that are known in the art. Methods employed for expanding and differentiating stem cells into endothelial cells can, for example, be such as those described in Li et al., *Stem Cells and Development.* 20:1701-1710 (2011).

In an embodiment, the stem and/or progenitor cells are allogenic cells. As used herein, the term "allogenic" denotes cells obtained from a genetically non-identical donor of the same species as the subject receiving the cells. The allogenic cells may be donated by a source unrelated to the subject, but preferably will be a very close relative, most preferably a family member of the subject, such as a parent or sibling of the subject.

In an embodiment, the stem and/or progenitor cells are autologous cells. As used herein, the term "autologous" denotes cells obtained from the same subject in need of treatment and/or prevention of diabetes mellitus. The use of autologous cells may provide certain advantages including the elimination of the need for immunosuppressive agents and/or avoidance of accidental transmission of infectious agents from another individual.

In an embodiment, upon harvesting and/or expansion of the cells in vitro, the cells are concentrated by brief centrifugation. The cells can be further washed and re-suspendend in a final, clinically usable solution such as saline, buffered saline or, alternatively, be re-suspendend in a freezing medium such as media plus dimethylsulfoxide, or any other suitable cryoprotectant, and frozen for storage.

The present disclosure also provides genetically modified stem and/or progenitor cells. In some embodiments, a stem and/or progenitor cell is genetically modified with: 1) an exogenous VEGF nucleic acid; 2) an exogenous ANG-2 nucleic acid; 3) an exogenous VCAM nucleic acid; 4) an exogenous HGF nucleic acid; 5) an exogenous CADHERIN nucleic acid; or 6) any combination of the above mentioned nucleic acids. The term "genetic modification" refers to a permanent or transient genetic change induced in a cell following the introduction of an exogenous nucleic acid sequence. An "exogenous nucleic acid sequence" is that which is not normally or naturally found in and/or produced by the cell in nature. In some embodiments, a cell is genetically modified in vitro. Methods of introducing a nucleic acid into a cell are known in the art, and any known method can be used to introduce a nucleic acid into a cell. Suitable methods include, e.g. infection, lipofection, electroporation, microinjection, calcium phosphate precipitation, DEAE-dextran mediated transfection, liposome-mediated transfection, and the like.

The present disclosure also contemplates an antigen-specific therapy with or without stem and/or progenitor cells.

In an embodiment of any of the above-described methods or compositions, the at least one antigen-specific therapy is an immunoglobulin-polypeptide chimera.

As used herein, the term "antigen-specific therapy" relates to treatment wherein immunoglobulins (Igs) are used to deliver self and altered self peptides for the suppression of pathological immune responses. The Igs genetically modified to express disease-specific peptides are referred to herein as "immunoglobulin-polypeptide chimeras" or "Ig-chimeras." Peptides corresponding to disease-specific T- or B-cell epitopes can be genetically modified into the Igs to cause downregulation of the pathogenic immune response and treat autoimmune diseases like T1D. Delivery of the Ig-chimeras significantly increases presentation to T cells relative to free peptide (Legge et al., *J. Exp. Med.* 191:2039-2051 (2011); Zaghouani et al., *Science.* 259:224-227 (1993)).

In still another embodiment of the disclosure, the immunoglobulin, or a portion thereon, can be human or humanized, such as, for example, human IgG, such as IgG1, IgG2, IgG2a, IgG2b, IgG3 and/or IgG4.

In some embodiments, the peptide is inserted within the variable region of the immunoglobulin, or a portion thereof, and the immunoglobulin, or a portion thereof, comprises human IgG or humanized IgG.

In still another embodiment, the peptide is inserted within at least one of the variable regions of the immunoglobulin, or a portion thereof, comprising the complementarity determining regions (CDR) CDR1, CDR2 and/or CDR3 region. Illustratively, the peptide is inserted within the CDR3 region of the immunoglobulin, or a portion thereof, by deleting the D segment and inserting the peptide. (Legge et al., *J. Exp. Med.,* 191:2039-2052 (2000); Legge et al., *J. Exp. Med.,* 196:217-227 (2002); Gregg et al., *J. Immunol.,* 173:7308-7316 (2004); Gregg et al., *J. Immunol.,* 174:662-670 (2005)). A skilled artisan can readily prepare large-scale transfectomas and purify the Ig-chimeras by column separation. (Jain et al., *J. Exp. Med.,* 205:207-218 (2008)).

In one embodiment, the antigen-specific therapy for the down regulation of diabetogenic T cells comprises an immunoglobulin, or a portion thereof, linked to a protein fragment or peptide. In yet another embodiment, the immunoglobulin, or portion thereof, can bind, or is capable of binding, to an Fc receptor.

In an embodiment of the disclosure, the immunoglobulin-polypeptide chimera comprises an immunoglobulin having a CDR3 region, and wherein a peptide is inserted within the CDR3 region.

In an embodiment, the peptide comprises a diabetogenic T cell epitope. In another embodiment, the peptide comprises a late-stage epitope, which is an epitope detected at an advanced stage of diabetes. In other embodiments, the peptide is derived from GAD65. In other embodiments, the peptide is derived from insulin. In other embodiments, the peptide is derived from IA-2. In other embodiments, the peptide is derived from ZnT8. In yet other embodiments the peptide is derived from IGRP.

In an embodiment, the diabetogenic epitope comprises GAD2 (SEQ ID NO: 1).

In an embodiment, the diabetogenic epitope comprises GAD1 (SEQ ID NO: 2).

In an embodiment, the diabetogenic epitope comprises INSβ. (SEQ ID NO: 3).

In some embodiments, the immunoglobulin is soluble, for example, solubilized Ig-GAD2, solubilized Ig-GAD1 or solubilized Ig-INSβ.

In yet another embodiment of the disclosure, the immunoglobulin-polypeptide chimera is aggregated. The chimeras can be aggregated by precipitation with 50%-saturated $(NH_4)_2SO_4$ as has been previously described in Chase et al., Methods in Immunology and Immunochemistry. 2: 249-341 (1968) or using other techniques known to those of skill in the art.

Methods of Treatment

Methods of treating or preventing diabetes mellitus in a subject, including administering to the subject a composition comprising an amount of one or more stem and/or progenitor cells and an amount of at least one antigen-specific therapy, are also contemplated by the present disclosure In an embodiment, cells are concentrated or diluted to an appropriate density which can be the same or different from the cell density for administration of the cells. The cells can be concentrated or diluted with an acceptable pharmaceutical carrier. The term "pharmaceutically acceptable carrier" as used herein refers to a diluent, adjuvant, excipient, or vehicle with which the stem and/or progenitor cells of the disclosure is administered and which is approved by a regulatory agency of the Federal or a state government or listed in the U.S. Pharmacopeia or other generally recognized pharmacopeia for use in animals, and more particularly in humans. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. When administered to a patient, the stem and/or progenitor cells and pharmaceutically acceptable carriers can be sterile. Water is a useful carrier when the stem and/or progenitor cells are administered intravenously. Saline solutions and aqueous dextrose and glycerol solutions can also be employed as liquid carriers, particularly for injectable solutions. Suitable pharmaceutical carriers also include excipients such as glucose, lactose, sucrose, glycerol monostearate, sodium chloride, glycerol, propylene, glycol, water, ethanol and the like. The present compositions, if desired, can also contain minor amounts of wetting or emulsifying agents, or pH buffering agents. The present compositions advantageously may take the form of solutions, emulsion, sustained-release formulations, or any other form suitable for use. The selection of a suitable carrier is within the skill of the ordinary artisan.

In an embodiment, the cells are concentrated to a density of about 1,000 to about 200,000 cells per microliter. In an embodiment, a density of about 5,000 to about 50,000 cells per microliter is used. In another embodiment, a density of about 10,000 to 30,000 cells per microliter is used.

Generally, a composition including stem and/or progenitor cells can be administered per dose in the range of $10^5$-$10^8$ cells per kg body weight, preferably in the range of $10^6$-$10^7$ cells per kg body weight. Cell dosage depends upon factors such as the site of injection, the route of administration, disease state, the minimum dose necessary for a beneficial effect, and toxicity side-effect considerations. A preferred administration schedule can be readily determined on a patient-specific basis by a skilled artisan.

The volume of solution (e.g., pharmaceutically acceptable carrier) in which the stem and/or progenitor cells are suspended for delivery to a treatment area can be referred to herein as the injection volume. The injection volume depends upon numerous factors, including the injection site, number of cells administered, and state of the disease. More specifically, the lower limit of the injection volume can be determined by practical liquid handling of viscous suspensions of high cell density as well as the tendency of the cells to cluster. The upper limit of the injection volume can be determined by limits of compression force exerted by the injection volume that are necessary to avoid injuring the host tissue, as well as the practical surgery time.

In an embodiment, the composition comprising an amount of stem and/or progenitor cells may be administered to a subject in accordance with known methods, such as intravenous administration, e.g., as a bolus or by continuous infusion over a period of time, by intramuscular, intraperitoneal, intracerebrospinal, subcutaneous, intra-articular, intrasynovial, intrathecal, oral, topical, or inhalation routes. Intravenous, intraperitoneal, or subcutaneous administration of the cells is preferred, with intravenous or intraperitoneal routes being particular preferred. The stem and/or progenitor cells may be administered by injection into the portal vein; however, other cell administration paradigms well known in the art can be used.

In one embodiment, compositions of stem and/or progenitor cells of the invention are formulated as an injectable formulation and comprise, for example, an aqueous solution or suspension of the active ingredient suitable for intravenous delivery. When preparing the composition for injection, particularly for intravenous delivery, a continuous phase can be present that comprises an aqueous solution of tonicity modifiers, buffered to a pH below about 7, or below about 6, for example about 2 to about 7, about 3 to about 6 or about 3 to about 5. The tonicity modifiers can comprise, for example, sodium chloride, glucose, mannitol, trehalose, glycerol, or other pharmaceutical agents that render osmotic pressure of the formulation isotonic with blood. Alternatively, when a larger quantity of the tonicity modifier is used in the formulation, it can be diluted prior to injection with a pharmaceutically acceptable diluent to render the mixture isotonic with blood.

In another embodiment, the compositions of the present invention are administered by intravenous (IV) infusion or intra-arterial administration over a desired period (for example, bolus injection, 5 min, 15 min, 30 min, 1 hr, 2 hr, 3 hr, 6 hr, 24 hr, 48 hr, 72 hr or 96 hour infusions). In one embodiment of the present invention the period of administration is no greater than about 3 hours.

In an embodiment, the treatment of the present disclosure with allogenic cell transplantation involves administration of a composition comprising one or more immunosuppressive agents to control rejection of the stem and/or progenitor cells. Preferred immunosuppressive agents include, but are not limited to, prednisone, methyl prednisolone, azathioprine, cyclophosphamide, cyclosporine, basiliximab, tacrolimus, mycophenolate mofetil, or sirolimus. Preparation and dosing schedules for such immunosuppressive agents may be used according to manufacturers' instructions or as determined empirically by the skilled practitioner.

In one embodiment of the present invention, the cells are administered once. In another embodiment, the cells are administered daily (or 1 to 5 times daily), weekly, or monthly. Illustratively, the cells are administered weekly for three weeks, and such administration achieves, for example, suppression of T1D. However, other administration schedules are operable herein. A preferred administration schedule depends on the particular subject being treated, the disease state, the type of stem and/or progenitor cell administered, and other factors well-known to a skilled practitioner.

In some embodiments of any of the aforementioned methods, the composition comprising an amount of stem and/or progenitor cells thereof is administered once. In some embodiments of any of the aforementioned methods, administration of an initial dose the composition comprising an amount of stem and/or progenitor cells thereof is followed by the administration of one or more subsequent doses. Examples of dosing regimens (e.g., an interval between the first dose and one or more subsequent doses) that can be used in the methods of the disclosure include an interval of about once every week to about once every 12 months, an interval of about once every two weeks to about once every 6 months, an interval of about once every month to about once every 6 months, an interval of about once every month to about once every 3 months, or an interval of about once every 3 months to about once every 6 months. In some embodiments, administration is monthly, every two months, every three months, every four months, every five months, every six months, or on recurrence of the T1D.

The present invention is also directed to a therapeutic method of treating or preventing T1D where treatment with an antigen-specific therapy is indicated.

In one embodiment of the present disclosure, an antigen-specific therapy is administered daily (or 1 to 5 times daily), weekly, or monthly. Illustratively, the composition is administered three times a week for five weeks and then weekly for an additional five weeks, and such administration achieves, for example, suppression of T1D.

A dosage and dosage regimen may be administered to provide the optimal desired response (e.g., therapeutic response). The dose of an antigen-specific therapy may be measured in units of mg/kg of patient body weight. Alternatively, the dose of antigen-specific therapy is measured in units of mg/kg of patient lean body weight (e.g., body weight minus body fat content), in units of mg/m$^2$ of patient body surface area, or in units of mg per dose (e.g., a fixed dose) administered to a patient. Any measurement of dose can be used in conjunction with the compositions and methods of the invention and dosage units can be converted by means standard in the art.

The method comprises the administration of an antigen-specific therapy of the present invention to a subject in need thereof. In one embodiment, the dosage regimen to prevent, give relief from, or ameliorate T1D corresponds to once-a-day or twice-a-day dosages, and can include, for example, about 0.0001 mg/kg, about 0.0005 mg/kg, about 0.001 mg/kg, about 0.01 mg/kg, about 0.05 mg/kg, about 0.1 mg/kg, about 0.5 mg/kg, about 1 mg/kg, about 2 mg/kg, about 5 mg/kg, about 10 mg/kg, about 15 mg/kg, about 20 mg/kg, about 30 mg/kg, about 40 mg/kg, about 50 mg/kg, about 60 mg/kg, about 70 mg/kg, about 80, mg/kg, about 90 mg/kg, about 100 mg/kg, about 110 mg/kg, about 120 mg/kg, about 130 mg/kg, about 140 mg/kg, about 150 mg/kg, about 160 mg/kg, about 170 mg/kg, about 180 mg/kg, about 190 mg/kg, about 200 mg/kg, about 220 mg/kg, about 240 mg/kg, about 250 mg/kg, about 500 mg/kg, about 750 mg/kg, or about 1,000 mg/kg (by body weight of the subject) dose of an antigen-specific therapy of the present invention, and can be modified in accordance with a variety of factors. These specific mg/kg amounts can vary, for example, from about 0.01% to about 20% or more, depending on the application and desired therapeutic result. Other factors include the type of subject, the age, weight, sex, diet, and medical condition of the subject and the severity of the disease. Thus, the dosage regimen actually employed can vary widely and therefore deviate from the dosage regimen set forth above.

An antigen-specific therapy for use in any of the aforementioned methods may be administered in one or more doses (e.g., an initial dose optionally followed by one or more subsequent doses). Those skilled in the art will appreciate that dosages are generally higher and/or frequency of administration greater for initial treatment as compared with maintenance regimens. In certain embodiments, two or more, three or more, four or more, five or more, six or more, seven or more, eight or more, nine or more, ten or more or eleven or more subsequent doses of the antibody are administered. The aforementioned dosage amounts refer to mg (antigen-specific therapy)/kg (weight of the individual to be treated).

An antigen-specific therapy thereof for use in any of the aforementioned methods may be administered as a fixed dose, independent of a dose per subject weight ratio.

In some embodiments, the antigen-specific therapy is administered in one or more fixed doses of about 1000 mg or less, 500 mg or less, or 250 mg or less, 100 mg or less, 90 mg or less, 80 mg or less, 70 mg or less, 60 mg or less, 50 mg or less, 40 mg or less, 30 mg or less, 20 mg or less, or 10 mg or less of antigen-specific therapy. In some embodiments, the antigen-specific therapy is administered in one or more doses of at least 0.5 mg, at least 1 mg of antigen-specific therapy, or at least 10 mg of antigen-specific therapy. In some embodiments, the antigen-specific therapy thereof is administered in one or more doses of 1 mg to 100 mg of antigen-specific therapy.

In certain embodiments, the fixed dose antigen-specific therapy is from about 1 mg to about 10 mg, about 1 mg to about 25 mg, about 10 mg to about 25 mg, about 10 mg to about 50 mg, about 10 mg to about 100 mg, about 25 mg to about 50 mg, about 25 mg to about 100 mg, about 50 mg to about 100 mg, about 50 mg to about 150 mg, about 100 mg to about 150 mg, about 100 mg to about 200 mg, about 150 mg to about 200 mg, about 150 mg to about 250 mg, about 200 mg to about 250 mg, about 200 mg to about 300 mg, about 250 mg to about 300 mg, about 250 mg to about 500 mg, about 300 mg to about 400 mg, about 400 mg to about 500 mg, about 400 mg to about 600 mg, about 500 mg to about 750 mg, about 600 mg to about 750 mg, about 700 mg to about 800 mg, or about 750 mg to about 1000 mg. In some embodiments, the fixed dose of antigen-specific therapy thereof is less than 100 mg.

In various embodiments, dosage units of the present invention contain, for example, about 1 ng to about 2000 mg, about 0.001 mg to about 750 mg, about 0.01 mg to about 500 mg, about 0.1 mg to about 300 mg or about 1 mg to about 100 mg of an antigen-specific therapy of the present invention. Illustratively, such unit dosage forms can contain about 0.001 mg, or about 0.01 mg, or about 0.1 mg, or about 1 mg, or about 2 mg, or about 5 mg, or about 10 mg, or about 15 mg, or about 20 mg, or about 30 mg, or about 40 mg, or about 50 mg, or about 60 mg, or about 70 mg, or about 80, mg, or about 90 mg, or about 100 mg, or about 110 mg, or about 120 mg, or about 130 mg, or about 140 mg, or about 150 mg, or about 160 mg, or about 170 mg, or about 180 mg, or about 190 mg, or about 200 mg, or about 300 mg, or about 400 mg, or about 500 mg, or about 750 mg, or about 1,000 mg of an antigen-specific therapy of the present invention.

Illustratively, dosage units each contain about 0.1 mg, about 1 mg, about 5 mg, about 10 mg, about 15 mg, about 20 mg, about 40 mg, about 80 mg, about 100 mg, about 250 mg, about 500 mg, or about 1000 mg of an antigen-specific therapy of the present invention. The dosage unit form can be selected to accommodate the desired frequency of administration used to achieve the specified daily dosage. In one embodiment, a composition of the invention will be administered to a subject in an amount sufficient to about 0.1 to about 15 mg, about 0.5 to about 10 mg, and or about 1 to about 5 mg of the active agent, for example Ig-GAD2, Ig-GAD1, etc.

In some embodiments of any of the aforementioned methods, the antigen-specific therapy is administered once to treat or prevent T1D. In some embodiments of any of the aforementioned methods, administration of an initial dose of the antigen-specific therapy is followed by the administration of one or more subsequent doses. Examples of dosing regimens (e.g., an interval between the first dose and one or more subsequent doses) that can be used in the methods of the disclosure include an interval of about once every week to about once every 12 months, an interval of about once every two weeks to about once every 6 months, an interval of about once every month to about once every 6 months, an interval of about once every month to about once every 3 months, or an interval of about once every 3 months to about once every 6 months. In some embodiments, administration is monthly, every two months, every three months, every four months, every five months, every six months, or on recurrence of T1D.

The disclosure also provides dosing regimens for use in any of the aforementioned methods, wherein the dosing regimens comprise more than one dosing interval for administration of the antigen-specific therapy. In some embodiments, the dosage regimen comprises at least two (e.g., two, three, four, five, six) different dosing intervals for administration of the antigen-specific therapy. In some embodiments, the dosage regimen comprises two different dosing intervals for administration of the antigen-specific therapy. In some embodiments, the dosing regimen comprises two different dosing intervals for administration of the antigen-specific therapy, wherein a first dosing interval comprises administration of one or more doses of the antigen-specific therapy thereof and a second dosing interval comprises administration of one or more doses of the antigen-specific therapy thereof, and wherein the first dosing interval is shorter in time than the second dosing interval. For example, the first dosing interval may be days or weeks, and the second dosing interval may be months. In some embodiments, the first dosing interval is about 5 days to about 28 days, about 7 days to about 21 days, about 12 days to about 16 days, or about 14 days. In some embodiments, the second dosing interval is about 1 month to about 3 months, about 1 month to about 2 months, or about 1 month.

In some embodiments of any of the aforementioned methods, the dose can be escalated or reduced to maintain a constant dose in the blood or in a tissue, such as, but not limited to, the pancreas. In related embodiments, the dose is escalated or reduced by about 2%, 5%, 8%, 10%, 15%, 20%, 30%, 40%, 50%, 60%, 70%, 80%, 90%, and 95% in order to maintain a desired level of the antigen-specific therapy.

In some embodiments of any of the aforementioned methods, the antigen-specific therapy are administered to a subject such that the interval between doses is a time sufficient to maintain a plasma concentration of said antigen-specific therapy in the subject at a level of at least about 0.1 µg/mL, at least about 0.3 µg/mL, at least about 1 µg/mL or at least about 2 µg/mL. In some embodiments, these plasma concentration values refer to values obtained for an individual that is treated with the antigen-specific therapy in accordance with the disclosure herein.

In some embodiments of any of the aforementioned methods, administration of an initial dose of the antigen-specific therapy is followed by the administration of one or more subsequent doses, and wherein said one or more subsequent doses are in an amount that is approximately the same or less than the initial dose.

In some embodiments of any of the aforementioned methods, administration of an initial dose of the antigen-specific therapy is followed by the administration of one or more subsequent doses, and wherein at least one of the subsequent doses is in an amount that is more than the initial dose.

In some embodiments of any of the aforementioned methods, an antigen-specific therapy is administered, wherein administration of an initial dose of the antigen-specific therapy is followed by the administration of one or more subsequent doses, and wherein the plasma concentration of said antigen-specific therapy in the human is permitted to decrease below a level of about 0.1 µg/mL, about 0.07 µg/mL, about 0.05 µg/mL, about 0.03 µg/mL or about 0.01 µg/mL for a period of time greater than about 1 week and less than about 6 months between administrations during a course of treatment with said initial dose and one or more subsequent doses. In some embodiments, the plasma concentration values refer to values obtained for an individual that is treated with the antigen-specific therapy in accordance with the disclosure herein.

The amount of antigen-specific therapy necessary to elicit a therapeutic effect can be experimentally determined based on, for example, the absorption rate of the antigen-specific therapy into the blood serum, the bioavailability of the antigen-specific therapy, and the degree of internalization and presentation of the peptide of the Ig-chimera. It is understood, however, that specific dose levels of the antigen-specific therapy of the present invention for any particular subject depends upon a variety of factors including the activity of the specific compound employed, the age, body weight, general health, sex, and diet of the subject (including, for example, whether the subject is in a fasting or fed state), the time of administration, the rate of excretion, the drug combination, the severity of the diabetes mellitus and form of administration. Treatment dosages generally may be titrated to optimize safety and efficacy. Typically, dosage-effect relationships from in vitro and/or in vivo tests initially can provide useful guidance on the proper doses for subject administration. Studies in animal models generally may be used for guidance regarding effective dosages for treatment of diabetic disorders or diseases in accordance with the present invention. In terms of treatment protocols, it should be appreciated that the dosage to be administered will depend on several factors, including the particular antigen-specific therapy that is administered, the route administered, the condition of the particular subject, etc. Generally speaking, one will desire to administer an amount of the antigen-specific therapy for a period of time that elicits a desired therapeutic effect, for example, lowering blood glucose level to acceptable levels, or improvement or elimination of symptoms, and other indicators as are selected as appropriate measures by those skilled in the art. Determination of these parameters is well within the skill of the art.

In some embodiments, the composition comprising the antigen-specific therapy may be administered to a subject in accordance with known methods, such as intravenous administration, e.g., as a bolus or by continuous infusion over a period of time, by intramuscular, intraperitoneal, intracerebrospinal, subcutaneous, intra-articular, intrasynovial, intrathecal, oral, topical, or inhalation routes. Intravenous, intraperitoneal, or subcutaneous administration of the cells is preferred, with intravenous or intraperitoneal routes being particular preferred.

In one embodiment, antigen-specific therapy of the invention is formulated as an injectable formulation and comprises, for example, an aqueous solution or suspension of the active ingredient suitable for intravenous delivery. When preparing the antigen-specific therapy for injection, particularly for intravenous delivery, a continuous phase can be present that comprises an aqueous solution of tonicity modifiers, buffered to a pH below about 7, or below about 6, for example about 2 to about 7, about 3 to about 6 or about 3 to about 5. The tonicity modifiers can comprise, for example, sodium chloride, glucose, mannitol, trehalose, glycerol, or other pharmaceutical agents that render osmotic pressure of the formulation isotonic with blood. Alternatively, when a larger quantity of the tonicity modifier is used in the formulation, it can be diluted prior to injection with a pharmaceutically acceptable diluent to render the mixture isotonic with blood.

In another embodiment, the antigen-specific therapy of the present invention are administered by intravenous (IV) infusion or intra-arterial administration over a desired period (for example, bolus injection, 5 min, 15 min, 30 min, 1 hr, 2 hr, 3 hr, 6 hr, 24 hr, 48 hr, 72 hr or 96 hour infusions). In one embodiment of the present invention the period of administration is no greater than about 3 hours.

In another embodiment of the present invention, the antigen-specific therapy of the invention is in the form of solid dosage forms, for example tablets (including but not limited to swallowable tablets, chewable tablets, suspension tablets, etc.), capsules, caplets, troches, lozenges, powders, granules, etc. Solid compositions are illustratively prepared by mixing the therapeutic agent with a pharmaceutical excipient to form a solid preformulation composition containing a homogeneous mixture of the therapeutic agent and excipient. When referring to these preformulation compounds as homogeneous, it is meant that the agents are substantially evenly distributed throughout the composition so that the composition may be readily subdivided into equally effective unit dosage forms, such as tablets, pills and capsules. This solid preformulation is then subdivided into unit dosage forms of the type described herein.

Compressed tablets are solid dosage forms prepared by compacting a formulation containing the antigen-specific therapy and excipient selected to aid the processing and improve the properties of the product. The term "compressed tablet" generally refers to a plain, uncoated tablet for oral ingestion, prepared by a single compression or by pre-compaction tapping followed by a final compression.

The solid dosage forms of the present invention may be coated or otherwise compounded to provide a dosage form affording the advantage of improved handling or storage characteristics. For example, a tablet or pill can comprise an inner dosage and an outer dosage component, the latter being in the form of an envelope over the former.

An antigen-specific therapy of the present invention can further comprise one or more pharmaceutically acceptable excipients. Suitable excipients are any of those commonly used excipients in pharmaceutics and should be selected on the basis of compatibility with the pharmaceutical agent and the release profile properties of the desired dosage form. Any suitable excipient can be present in a composition of the invention in an amount of about 1% to about 80%, about 2% to about 70%, about 3% to about 60%, about 4% to about 50%, or about 5% to about 40%, by weight.

Illustrative classes of pharmaceutical excipients include binders, disintegrants, filling agents, surfactants, solubilizers, stabilizers, preservatives, lubricants, wetting agents, diluents, tableting agents, glidants, etc.

In one embodiment, a composition of the invention comprises a preservative. Illustrative preservatives include benzalkonium chloride, propylparabem, butylparaben, chlorobutanol, benzyl alcohol, phenol, sodium benzoate, or EDTA.

Illustrative binders include acacia, alginic acid and salts thereof, cellulose derivatives, methylcellulose, hydroxyethyl cellulose, hydroxypropyl cellulose, magnesium aluminum silicate, polyethylene glycol, gums, polysaccharide acids, bentonites, hydroxypropyl methylcellulose, gelatin, polyvinylpyrrolidone, polyvinylpyrrolidone/vinyl acetate copolymer, crospovidone, povidone, polymethacrylates, hydroxypropylmethylcellulose, hydroxypropylcellulose, starch, pregelatinized starch, ethylcellulose, tragacanth, dextrin, microcrystalline cellulose, sucrose, or glucose, and the like.

Illustrative disintegrants (also referred to as disintegration agents) include starches, pregelatinized corn starch, pregelatinized starch, celluloses, cross-linked carboxymethylcellulose, sodium starch glycolate, crospovidone, cross-linked polyvinylpyrrolidone, croscarmellose sodium, a calcium, a sodium alginate complex, clays, alginates, gums, or sodium starch glycolate, and any disintegration agents used in solid preparations.

Illustrative filling agents include lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

Illustrative surfactants include sodium lauryl sulfate, sorbitan monooleate, polyoxyethylene sorbitan monooleate, polysorbates, polaxomers, bile salts, glyceryl monostearate, Pluronic™ line (BASF), and the like.

Illustrative solubilizers include citric acid, succinic acid, fumaric acid, malic acid, tartaric acid, maleic acid, glutaric acid sodium bicarbonate and sodium carbonate and the like.

Illustrative stabilizers such as antioxidation agents, buffers, or acids, and the like, can also be utilized.

Illustrative lubricants include magnesium stearate, calcium hydroxide, talc, sodium stearyl fumarate, hydrogenated vegetable oil, stearic acid, glyceryl behapate, magnesium, calcium and sodium stearates, stearic acid, talc, waxes, Stearowet, boric acid, sodium benzoate, sodium acetate, sodium chloride, DL-leucine, polyethylene glycols, sodium oleate, or sodium lauryl sulfate, and the like.

Illustrative wetting agents include oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, or sodium lauryl sulfate, and the like Illustrative diluents include lactose, starch, mannitol, sorbitol, dextrose, microcrystalline cellulose, dibasic calcium phosphate, sucrose-based diluents, confectioner's sugar, monobasic calcium sulfate monohydrate, calcium sulfate dihydrate, calcium lactate trihydrate, dextrates, inositol, hydrolyzed cereal solids, amylose, powdered cellulose, calcium carbonate, glycine, or bentonite, and the like.

Illustrative anti-adherents or glidants include talc, corn starch, DL-leucine, sodium lauryl sulfate, and magnesium, calcium, or sodium stearates, and the like.

Illustrative pharmaceutically compatible carriers include acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, or pregelatinized starch, and the like.

Additionally, drug formulations are discussed in, for example, Hoover, John E., *Remington's Pharmaceutical Sciences*, Mack Publishing Co., Easton, Pa. 1975. Another discussion of drug formulations can be found in Liberman, H. A. and Lachman, L., Eds., *Pharmaceutical Dosage Forms*, Marcel Decker, New York, N.Y., 1980.

In making compositions of the present invention, the individual components can be mixed with a pharmaceutically acceptable excipient, diluted by the excipient or enclosed within a capsule, sachet, paper or other container.

When an excipient serves as a diluent, it can be a solid, semi-solid or liquid material, which acts as a vehicle, carrier or medium for the active ingredient. Thus, the compositions can be in the form of a tablet, pill, powder, lozenge, sachet, cachet, elixir, troche, suspension, emulsion, solution, syrup, aerosol (as a solid or in a liquid medium), soft and hard gelatin capsule, sterile packaged powder, dispensable powder, granule, or liquid.

In one embodiment of the present invention, the manufacturing processes may employ one or a combination of methods: (1) dry mixing, (2) direct compression, (3) milling, (4) dry or non-aqueous granulation, (5) wet granulation, or (6) fusion. Lachman et al., *The Theory and Practice of Industrial Pharmacy* (1986). Such tablets may also comprise film coatings, which disintegrate upon oral ingestion or upon contact with diluent.

Initial treatment of a subject suffering from diabetes mellitus where treatment with an antigen-specific therapy is indicated can begin with the dosages indicated above. Treatment is generally continued as necessary over a period of hours, days, weeks to several months or years until the condition or disorder has been controlled or eliminated. In one embodiment, a composition of the invention can be administered to a subject in a plurality of dosages. Illustratively, such administration can comprise a continuous (for example, by administration by an osmotic pump, patch, gel, cream, or infusion device), hourly, daily, weekly, bi-weekly, or monthly administration of the composition for any desired duration, for example for a period of about 1 week, about 2 weeks, about 1 month or more, about 3 months or more, about 6 months or more, about 9 months or more, about 1 year or more, about 3 years or more, about 5 years or more, or throughout the subject's life.

Subjects undergoing treatment with the antigen-specific therapy disclosed herein can be routinely monitored by any of the methods well known in the art to determine the effectiveness of therapy. Continuous analysis of such data permits modification of the treatment regimen during therapy so that optimal effective amounts of antigen-specific therapy of the present invention are administered at any point in time, and so that the duration of treatment can be determined as well. In this way, the treatment regimen/dosing schedule can be rationally modified over the course of therapy so that the lowest amount of an antigen-specific therapy exhibiting satisfactory effectiveness is administered, and so that administration is continued only so long as is necessary to successfully treat the condition or disorder.

In some embodiments, the stem and/or progenitor cells and the antigen-specific therapy may be co-administered. The stem and/or progenitor cells and the antigen-specific therapy which make up the therapy may be a combined dosage form or in separate dosage forms intended for substantially simultaneous administration. The stem and/or progenitor cells and the antigen-specific therapy may also be administered sequentially, with either the stem and/or progenitor cells and the antigen-specific therapy being administered by a regimen calling for multiple step administration.

Thus, a regimen may call for sequential administration of stem and/or progenitor cells and the antigen-specific therapy with spaced-apart administration of the separate, active agents. The time period between the multiple administration steps may range from, for example, a few minutes to several hours to days, depending upon the properties of the stem and/or progenitor cells and the antigen-specific therapy such as potency, solubility, bioavailability, plasma half-life and kinetic profile of the therapeutic compound, as well as depending upon the effect of food ingestion and the age and condition of the subject. Circadian variation of the target molecule concentration may also determine the optimal dose interval. The stem and/or progenitor cells and the antigen-specific therapy whether administered simultaneously, substantially simultaneously, or sequentially, may involve a regimen calling for administration of the stem and/or progenitor cells by intravenous route and the antigen-specific therapy by an oral route, a percutaneous route, an intravenous route, an intramuscular route, or by direct absorption through mucous membrane tissues, for example. Whether the stem and/or progenitor cells and the antigen-specific therapy are administered orally, by inhalation spray, rectally, topically, buccally (for example, sublingual), or parenterally (for example, subcutaneous, intramuscular, intravenous and intradermal injections, or infusion techniques), separately or together, each such therapeutic compound will be contained in a suitable pharmaceutical formulation of pharmaceutically-acceptable excipients, diluents or other formulations components.

Combinations

The present methods can also be used in combination ("combination therapy") with another pharmaceutical agent that is indicated for treating, preventing, suppressing or delaying the onset of T1D, such as, for example, insulin, an alpha-glucosidase inhibitor, an insulin sensitizer, an antibody, or a hyperglycemic agent, which are commonly administered to treat the symptoms and/or complications related to this disorder. A combination therapy with antibodies for treating, preventing, suppressing or delaying the onset of T1D, include, for example, a short-course anti-CD3 monoclonal antibody therapy. These drugs have certain disadvantages associated with their use. Some of these drugs are not completely effective in the treatment of the aforementioned conditions and/or produce adverse side effects, such as hypoglycemia, microvascular disease, and macrovascular disease. However, when used in conjunction with the present invention, that is, in combination therapy, many if not all of these unwanted side effects may be reduced or eliminated. The reduced side effect profile of these drugs is generally attributed to, for example, the reduce dosage necessary to achieve a therapeutic effect with the administered combination.

As used herein, the phrase "combination therapy" refers to the administration of an amount of one or more stem and/or progenitor cells and an amount of at least one antigen-specific therapy in conjunction with another pharmaceutical agent.

The phrase "combination therapy" embraces the administration of a composition of the present invention in conjunction with another pharmaceutical agent that is indicated for treating or preventing T1D in a subject, as part of a specific treatment regimen intended to provide a beneficial effect from the co-action of these therapeutic agents for the treatment of T1D. The beneficial effect of the combination includes, but is not limited to, pharmacokinetic or pharmacodynamic co-action resulting from the combination of therapeutic agents. Administration of these therapeutic agents in combination typically is carried out over a defined time period (usually substantially simultaneously, minutes, hours, days, weeks, months or years depending upon the combination selected). "Combination therapy" generally is not intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, where each therapeutic agent is administered at a different time, as well as administration of these therapeutic agents, or at least two of the therapeutic agents, in a substantially simultaneous manner. Substantially simultaneous administration can be accomplished, for example, by administering to the subject a single injection, tablet or capsule having a fixed ratio of each therapeutic agent or in multiple, single injections, capsules, or tablets for each of the therapeutic agents. Sequential or substantially simultaneous administration of each therapeutic agent can be implemented by any appropriate route. For example, the composition of the present invention can be administered orally, percutaneously, intravenously, intramuscularly, and/or directly absorbed through mucosal membranes while the other therapeutic agent or agents of the combination can be administered by any appropriate route for that particular agent or agents, including, but not limited to, an oral route, a percutaneous route, an intravenous route, an intramuscular route, or by direct absorption through mucous membrane tissues. The sequence in which the therapeutic agents are administered is not narrowly critical. "Combination therapy" also can embrace the administration of the therapeutic agents as described above in further combination with other biologically active ingredients, such as, but not limited to, (1) antiinflammatory agents, such as a steroidal or nonsteroidal antiinflammatory drug, and/or a 5-lipoxygenase inhibitor; or (2) an agent for treating cardiovascular disease or disorders, such as, for example, an antihypertensive agent, including, for example, an angiotensin converting enzyme inhibitor (ACE-inhibitor), an alpha-adrenergic agonist, a beta-adrenergic agonist, an alpha-adrenergic blocker, an angiotensin II receptor antagonist; a diuretic, including, for example, an aldosterone antagonist, a benzothiadiazine derivative, an organomercurial, a purine, a steroid (for example, canrenone, oleandrin, spironolactone), a sulfonamide derivative, or a uracil; an antianginal agent; an antiarrhythmic agent; an antiarteriosclerotic agent; an antihyperlipoproteinemic agent; an anicholelithogenic agent; an anticholesteremic agent; an antihypercholesterolemic agent; an antihyperlipidemic agent; an antihypertensive agent; an antihypotensive agent; an antilipidemic agent; a calcium channel blocker; a cardiac depressant agent; a dopamine receptor agonist; a dopamine receptor antagonist; a HMG CoA reductase inhibitor; an hypocholesteremic agent; a hypolipidemic agent; a hypotensive agent; a monoamine oxidase inhibitor; a muscle relaxant; a potassium channel activator; a pressor agent; a serotonin uptake antagonist; a thrombolytic agent; a vasodilator agent; a vasopressor agent; or a vasoprotectant agent (Based in part upon the list provided in *The Merck Index*, Merck & Co. Rahway, N.J. (2001), which is hereby incorporated by reference); and with non-drug therapies, such as, but not limited to, surgery.

The therapeutic compounds which make up the combination therapy may be a combined dosage form or in separate dosage forms intended for substantially simultaneous administration. The therapeutic compounds that make up the combination therapy may also be administered sequentially, with either therapeutic compound being administered by a regimen calling for two step administration. Thus, a regimen may call for sequential administration of the therapeutic compounds with spaced-apart administration of the separate, active agents. The time period between the multiple administration steps may range from, for example, a few minutes to several hours to days, depending upon the properties of each therapeutic compound such as potency, solubility, bioavailability, plasma half-life and kinetic profile of the therapeutic compound, as well as depending upon the effect of food ingestion and the age and condition of the subject. Circadian variation of the target molecule concentration may also determine the optimal dose interval. The therapeutic compounds of the combined therapy whether administered simultaneously, substantially simultaneously, or sequentially, may involve a regimen calling for administration of one therapeutic compound by oral route and another therapeutic compound by an oral route, a percutaneous route, an intravenous route, an intramuscular route, or by direct absorption through mucous membrane tissues, for example. Whether the therapeutic compounds of the combined therapy are administered orally, by inhalation spray, rectally, topically, buccally (for example, sublingual), or parenterally (for example, subcutaneous, intramuscular, intravenous and intradermal injections, or infusion techniques), separately or together, each such therapeutic compound will be contained in a suitable pharmaceutical formulation of pharmaceutically-acceptable excipients, diluents or other formulations components.

Compositions comprising an amount of one or more stem and/or progenitor cells and an amount of at least one antigen-specific therapy are contemplated by the present disclosure.

As used herein, the term "composition" or "compositions" refers to the stem and/or progenitor cells alone, an antigen-specific therapy alone, or a combination of the stem and/or progenitor cells and the antigen-specific therapy.

Stem and/or progenitor cells and antigen-specific therapies can be formulated in compositions, especially pharmaceutical compositions, for use in the methods disclosed herein. Such compositions comprise an amount (e.g., a therapeutically or prophylactically effective amount) of a stem and/or progenitor cell and antigen-specific therapy thereof in a mixture with a suitable carrier, e.g., a pharmaceutically acceptable agent. Typically, stem and/or progenitor cells and antigen-specific therapies thereof are sufficiently purified for administration to an animal (e.g., human) before formulation in a pharmaceutical composition.

Pharmaceutically acceptable agents include for example, carriers, excipients, diluents, antioxidants, preservatives, coloring, flavoring and diluting agents, emulsifying agents, suspending agents, solvents, fillers, bulking agents, buffers, delivery vehicles, tonicity agents, cosolvents, wetting agents, complexing agents, buffering agents, antimicrobials, and surfactants.

Neutral buffered saline or saline mixed with albumin are exemplary appropriate carriers. The pharmaceutical compositions can include antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics, or polyethylene glycol (PEG). Also by way of example, suitable tonicity enhancing agents include alkali metal halides (preferably sodium or potassium chloride), mannitol, sorbitol, and the like. Suitable preservatives include benzalkonium chloride, thimerosal, phenethyl alcohol, methylparaben, propylparaben, chlorhexidine, sorbic acid and the like. Hydrogen peroxide also can be used as preservative. Suitable cosolvents include glycerin, propylene glycol, and PEG. Suitable complexing agents include caffeine, polyvinylpyrrolidone, beta-cyclodextrin or hydroxy-propyl-beta-cyclodextrin. Suitable surfactants or wetting agents include sorbitan esters, polysorbates such as polysorbate 80, tromethamine, lecithin, cholesterol, tyloxapal, and the like. The buffers can be conventional buffers such as acetate, borate, citrate, phosphate, bicarbonate, or Tris-HCl. Acetate buffer may be about pH 4-5.5, and Tris buffer can be about pH 7-8.5. Additional pharmaceutical agents are set forth in Remington's Pharmaceutical Sciences, 18th Edition, A. R. Gennaro, ed., Mack Publishing Company, 1990.

The composition can be in liquid form or in a lyophilized or freeze-dried form and may include one or more lyoprotectants, excipients, surfactants, high molecular weight structural additives and/or bulking agents (see for example U.S. Pat. Nos. 6,685,940, 6,566,329, and 6,372,716). In one embodiment, a lyoprotectant is included, which is a non-reducing sugar such as sucrose, lactose or trehalose. The amount of lyoprotectant generally included is such that, upon reconstitution, the resulting formulation will be isotonic, although hypertonic or slightly hypotonic formulations also may be suitable. In addition, the amount of lyoprotectant should be sufficient to prevent an unacceptable amount of degradation and/or aggregation of the protein upon lyophilization. Exemplary lyoprotectant concentrations for sugars (e.g., sucrose, lactose, trehalose) in the pre-lyophilized formulation are from about 10 mM to about 400 mM. In another embodiment, a surfactant is included, such as for example, nonionic surfactants and ionic surfactants such as polysorbates (e.g. polysorbate 20, polysorbate 80); poloxamers (e.g. poloxamer 188); poly (ethylene glycol) phenyl ethers (e.g. Triton); sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristarnidopropyl-, palmidopropyl-, or isostearamidopropyl-dimethylamine; sodium methyl cocoyl-, or disodium methyl ofeyl-taurate; and the MONAQUAT™ series (Mona Industries, Inc., Paterson, N.J.), polyethyl glycol, polypropyl glycol, and copolymers of ethylene and propylene glycol (e.g. Pluronics, PF68, etc). Exemplary amounts of surfactant that may be present in the pre-lyophilized formulation are from about 0.001-0.5%. High molecular weight structural additives (e.g. fillers, binders) may include for example, acacia, albumin, alginic acid, calcium phosphate (dibasic), cellulose, carboxymethylcellulose, carboxymethylcellulose sodium, hydroxyethylcellulose, hydroxypropylcellulose, hydroxypropylmethylcellulose, microcrystalline cellulose, dextran, dextrin, dextrates, sucrose, tylose, pregelatinized starch, calcium sulfate, amylose, glycine, bentonite, maltose, sorbitol, ethylcellulose, disodium hydrogen phosphate, disodium phosphate, disodium pyrosulfite, polyvinyl alcohol, gelatin, glucose, guar gum, liquid glucose, compressible sugar, magnesium aluminum silicate, maltodextrin, polyethylene oxide, polymethacrylates, povidone, sodium alginate, tragacanth microcrystalline cellulose, starch, and zein.

Exemplary concentrations of high molecular weight structural additives are from 0.1% to 10% by weight. In other embodiments, a bulking agent (e.g., mannitol, glycine) may be included.

Compositions can be suitable for parenteral administration. Exemplary compositions are suitable for injection or infusion into an animal by any route available to the skilled worker, such as intraarticular, subcutaneous, intravenous, intramuscular, intraperitoneal, intracerebral (intraparenchymal), intracerebroventricular, intramuscular, intraocular, intraarterial, intralesional, intrarectal, transdermal, oral, and inhaled routes. A parenteral formulation typically will be a sterile, pyrogen-free, isotonic aqueous solution, optionally containing pharmaceutically acceptable preservatives.

Aqueous carriers include water, alcoholic/aqueous solutions, emulsions or suspensions, including saline and buffered media. Examples of non-aqueous solvents are propylene glycol, polyethylene glycol, vegetable oils such as olive oil, and injectable organic esters such as ethyl oleate. Parenteral vehicles include sodium chloride solution, Ringers' dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, antimicrobials, anti-oxidants, chelating agents, inert gases and the like. See generally, Remington's Pharmaceutical Science, 16th Ed., Mack Eds., 1980, which is incorporated herein by reference.

Pharmaceutical compositions described herein can be formulated for controlled or sustained delivery in a manner that provides local concentration of the product (e.g., bolus, depot effect) sustained release and/or increased stability or half-life in a particular local environment. The invention contemplates that in certain embodiments such compositions may include a significantly larger amount of stem and/or progenitor cells and antigen-specific therapies, while the effective amount of stem and/or progenitor cells and antigen-specific therapies actually released and available at any point in time for is in accordance with the disclosure herein an amount much lower than the initial deposit. The compositions can include the formulation of stem and/or progenitor cells and antigen-specific therapies thereof, with particulate preparations of polymeric compounds such as polylactic acid, polyglycolic acid, etc., as well as agents such as a biodegradable matrix, injectable microspheres, microcapsular particles, microcapsules, bioerodible particles beads, liposomes, and implantable delivery devices that provide for the controlled or sustained release of the active agent which then can be delivered as a depot injection. Techniques for formulating such sustained- or controlled-delivery means are known and a variety of polymers have been developed and used for the controlled release and delivery of drugs. Such polymers are typically biodegradable and biocompatible. Polymer hydrogels, including those formed by complexation of enantiomeric polymer or polypeptide segments, and hydrogels with temperature or pH sensitive properties, may be desirable for providing drug depot effect because of the mild and aqueous conditions involved in trapping bioactive protein agents (e.g., antibodies). See, for example, the description of controlled release porous polymeric microparticles for the delivery of pharmaceutical compositions in PCT Application Publication WO 93/15722.

Suitable materials for this purpose include polylactides (see, e.g., U.S. Pat. No. 3,773,919), polymers of poly-(a-hydroxycarboxylic acids), such as poly-D-(-)-3-hydroxybutyric acid (EP 133,988A), copolymers of L-glutamic acid and gamma ethyl-L-glutamate (Sidman et al., *Biopolymers*, 22: 547-556 (1983)), poly (2-hydroxyethyl-methacrylate) (Langer et al., *J. Biomed. Mater. Res.*, 15: 167-277 (1981), and Langer, Chem. Tech., 12: 98-105 (1982)), ethylene vinyl acetate, or poly-D(-)-3-hydroxybutyric acid. Other biodegradable polymers include poly(lactones), poly(acetals), poly(orthoesters), and poly(orthocarbonates). Sustained-release compositions also may include liposomes, which can be prepared by any of several methods known in the art (see, e.g., Eppstein et al., *Proc. Natl. Acad. Sci. USA*, 82:3688-92 (1985)). The carrier itself, or its degradation products, should be nontoxic in the target tissue and should not further aggravate the condition. This can be determined by routine screening in animal models of the target disorder or, if such models are unavailable, in normal animals.

Certain formulations containing stem and/or progenitor cells and antigen-specific therapies thereof can be administered orally. Formulations administered in this fashion can be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents can be included to facilitate absorption of a selective binding agent. Diluents, flavorings, low melting point waxes, vegetable oils, lubricants, suspending agents, tablet disintegrating agents, and binders also can be employed.

Another preparation can involve an effective quantity of a stem and/or progenitor cell and antigen-specific therapy thereof in a mixture with non-toxic excipients which are suitable for the manufacture of tablets. By dissolving the tablets in sterile water, or another appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Suitable and/or preferred pharmaceutical formulations can be determined in view of the present disclosure and general knowledge of formulation technology, depending upon the intended route of administration, delivery format, and desired dosage. Regardless of the manner of administration, an effective dose can be calculated according to patient body weight, body surface area, or organ size. Further refinement of the calculations for determining the appropriate dosage for treatment involving each of the formulations described herein are routinely made in the art and is within the ambit of tasks routinely performed in the art. Appropriate dosages can be ascertained through use of appropriate dose-response data.

The pharmaceutical compositions can comprise stem and/or progenitor cells and antigen-specific therapies thereof in combination with other active agents (e.g., other than stem and/or progenitor cells and antigen-specific therapies thereof). Alternatively, the pharmaceutical compositions can comprise stem and/or progenitor cells and antigen-specific therapies thereof in combination with other pharmaceutical compositions, including, for example, pharmaceutical compositions comprising one or more active agents (e.g., other than stem and/or progenitor cells and antigen-specific therapies thereof). Such combinations are those useful for their intended purpose. The combinations which are part of this invention can be stem and/or progenitor cells and antigen-specific therapies, such as for example those described herein, and at least one additional agent. Examples of active agents that may be used in combination set forth below are illustrative for purposes and not intended to be limited. The combination can also include more than one additional agent, (e.g., two or three additional agents) if the combination is such that the formed composition can perform its intended function.

The disclosure further contemplates that additional pharmaceutical compositions comprising one or more other active agents may be administered separately from the stem and/or progenitor cells and antigen-specific therapies thereof (e.g., concurrent treatment regimen, subject receiving concurrent treatment), and such separate administrations may be performed at the same time or at different times, such as for example the same or different days, or different times of the same day. Administration of the other pharmaceutical compositions and/or active agents may be according to standard medical practices known in the art, or the administration may be modified (e.g., longer intervals between doses, smaller dosage levels, delayed initiation) when used in conjunction with administration of stem and/or progenitor cells and antigen-specific therapies thereof, such as disclosed herein.

In some embodiments, active agents may include antimicrobial agents including, for example, antibiotics such as a penicillin (e.g., penicillin, amoxicillin, benzylpenicillin, ampicillin, augmentin), a polyketide antibiotic (e.g., a macrolide, azithromycin, erythromycin, clarithromycin), a cephalosporin (e.g., cefadroxil, cefixime, cephalexin), a lincosamide (e.g., clindamycin), a quinolone (e.g., ciprofloxacin, levofloxacin, moxifloxacin), a folic acid synthesis inhibitor (e.g., a dihydrofolate reductase inhibitor, trimethoprim, dapsone, co-trimoxazole), a tetracycline (e.g., tetracycline, minocycline, doxycycline, demeclocycline, oxytetracycline), a rifamycin (e.g., rifampicin, rifabutin, rifapentine), a sulfonamide (e.g., sulfamethoxazole, sulfacetamide), an aminoglycoside (e.g., neomycin, amikacin, tobramycin), fusidic acid, a polypeptide antibiotic (e.g., bacitracin, polymixin B), a lipopeptide antibiotic (e.g., daptomycin), chloramphenicol and mupirocin.

It is further contemplated that the stem and/or progenitor cells and antigen-specific therapy thereof administered to a subject in accordance with the disclosure may be administered in combination (e.g., concurrently) with treatment with at least one additional pharmaceutical composition (e.g., comprising an active agent), such as for example any of the aforementioned active agents. In one embodiment, treatment with the at least one active agent is maintained. In another embodiment, treatment with the at least one active agent is reduced (e.g., tapered) or discontinued (e.g., when the subject is stable) during the course treatment (e.g., with the stem and/or progenitor cell and antigen-specific therapy thereof maintained at a constant dosing regimen). In another embodiment, treatment with the at least one active agent is reduced (e.g., tapered) or discontinued (e.g., when the subject is stable), and treatment with the stem and/or progenitor cell and antigen-specific therapy thereof is reduced (e.g., lower dose, less frequent dosing, shorter treatment regimen). In another embodiment, treatment with the at least one active agent is reduced (e.g., tapered) or discontinued (e.g., when the subject is stable), and treatment with the stem and/or progenitor cell and antigen-specific therapy thereof is increased (e.g., higher dose, more frequent dosing, longer treatment regimen). In yet another embodiment, treatment with the at least one active agent is maintained and treatment with the stem and/or progenitor cell and antigen-specific therapy thereof is reduced or discontinued (e.g., lower dose, less frequent dosing, shorter treatment regimen). In yet another embodiment, treatment with the at least one active agent and treatment with the stem and/or progenitor cell and antigen-specific therapy thereof are reduced or discontinued (e.g., lower dose, less frequent dosing, shorter treatment regimen).

In some embodiments, reducing the treatment with at least one active agent (e.g., other than stem and/or progenitor cells and antigen-specific therapy thereof) is a reduction in the cumulative amount of active agent administered during a course of treatment. In some embodiments, reducing the treatment with at least one active agent (e.g., other than stem and/or progenitor cells and antigen-specific therapy thereof) is a reduction in the actual dose amount of active agent administered. In some embodiments, reducing the treatment with at least one active agent provides a reduction in systemic immunosuppression.

The pharmaceutical compositions used in the disclosure may include a therapeutically effective amount or a prophylactically effective amount of the stem and/or progenitor cells and antigen-specific therapies thereof. A therapeutically effective amount refers to an amount effective, at dosages and for periods of time necessary, to achieve the desired therapeutic result. A therapeutically effective amount of the stem and/or progenitor cells and antigen-specific therapy may vary according to factors such as the disease state, age, sex, and weight of the individual, and the ability of the antibody or antibody portion to elicit a desired response in the individual. A therapeutically effective amount is also one in which any toxic or detrimental effects of the stem and/or progenitor cells and antigen-specific therapy are outweighed by the therapeutically beneficial effects. A prophylactically effective amount refers to an amount effective, at dosages and for periods of time necessary, to achieve the desired prophylactic result.

A therapeutically or prophylactically effective amount of a pharmaceutical composition comprising stem and/or progenitor cells and an antigen-specific therapy thereof will depend, for example, upon the therapeutic objectives such as the indication for which the composition is being used, the route of administration, and the condition of the subject. Pharmaceutical compositions are administered in a therapeutically or prophylactically effective amount to treat or prevent diabetes mellitus.

Without further description, it is believed that one of ordinary skill in the art may, using the preceding description and the following illustrative examples, make and utilize the agents of the present disclosure and practice the claimed methods. The following working examples are provided to facilitate the practice of the present disclosure, and are not to be construed as limiting in any way the remainder of the disclosure.

EXAMPLES

The present invention is further illustrated by the following examples, which should not be construed as limiting in any way. The materials and methods as used in the following experimental examples are described below.

Example 1

Materials and Methods

The following materials and methods were employed in the examples provided below. It will be apparent that where appropriate such materials and methods can be substituted for other known materials and methods to achieve the same intended purpose and/or result.

Animal Model

NOD and NOD-GFP (expressing the green fluorescence protein under the β-actin promoter) mice were previously described in Wallet et al., *Proc. Natl. Acad. Sci.* 106:24810-4815 (2009). All mice are maintained in an animal facility for the duration of the experiments and the experimental procedures performed on these animals are carried out according to the guidelines of the institutional Animal Care and Use Committee.

Assessment of Diabetes

Mice are bled from the tail vein weekly and the blood samples are used to assess for both glucose content and anti-insulin antibodies. For measurement of glucose, a drop of blood is directly placed on a test strip and the glucose content is read using an Accu-Chek Advantage monitoring system (Roche Diagnostics, Indianapolis, Ind.). For detection of anti-insulin antibodies the blood is allowed to coagulate for 1 hour at room temperature and the serum is separated and used for ELISA. Blood glucose level (BGL) monitoring begins at 10 weeks of age. A mouse is considered diabetic when the blood glucose is above 300 mg/dL for two consecutive weeks.

Peptides and Ig-Chimera

All peptides are purified by HPLC to >90% purity. The GAD2 peptide (SEQ ID NO: 1) corresponds to amino acid residues 206-220 of Glutamic Acid Decarboxylase-65 (GAD). The Ig-GAD2 chimera is created by inserting the GAD2 peptide sequence within the variable region of the CDR3 region of the heavy chain variable region of the 91A3 IgG2b, κ Ig The fusion heavy chain gene is then transfected along with the parental κ light chain gene for expression as a complete self-Ig molecule (Legge et al., *J. Exp. Med.*, 191:2039-2052 (2000); Legge et al., *J. Exp. Med.*, 196:217-227 (2002); Gregg et al., *J. Immunol.*, 173:7308-7316 (2004); Gregg et al., *J. Immunol.*, 174:662-670 (2005)). Large-scale cultures of transfectoma cells are performed in DME media and purified with sepharose beads (Jain et al., *J. Exp. Med.*, 205:207-218 (2008). Other peptides derived from GAD or the human insulin protein (alpha and beta chains) are within the scope of the present invention.

Treatment with Ig-GAD2 and Donor BM or Donor EPC

Mice determined to be diabetic are first given 2 sustained release insulin implants (LinShin, Toronto, Ontario, Canada) inserted subcutaneously in the abdomen to temporarily maintain normoglycemia for 2-3 weeks. The mice are then given 300 μg Ig-GAD2 intraperitoneal (i.p.) 3 times weekly for 5 weeks and then once a week for another 5 weeks. Donor BM cells are isolated from the femur and tibia of healthy (non diabetic) NOD mice and $10 \times 10^6$ cells are transferred intravenously (i.v.) weekly on week 2, 3, and 4 post diagnosis. The mice are monitored for BGL until day 120. The same treatment regimen is given to mice treated with endothelial progenitor cells (EPCs) except that FLK-1+ EPCs are given at $5 \times 10^4$ cells per injection while FLK-t EPCs are given at $3 \times 10^6$ cells per injection. To isolate EPCs, BM is harvested from healthy or diabetic mice and Lin⁻ cells are isolated using the lineage cell depletion kit according to manufacturer's instruction (Mitenyi Biotec). The Lin⁻ cells are stained with anti-c-Kit, anti-FLK-1 and 7-AAD and appropriately sorted.

Flow Cytometry Analyses

Samples are stained for detection of cell surface markers PECAM1 (PE-cy7-conjugated anti-PECAM1; eBiosciences), FLK-1 (APC-conjugated anti-FLK1; eBiosciences), c-Kit (PE-cy7-conjugated anti-c-Kit; BD Biosciences) and CD45 (APC-conjugated anti-CD45; BD Biosciences). For detection of apoptotic cells, cells are stained with 7-AAD (EMD Biosciences). For detection of intracellular IFNγ, IL-10, and IL-17 in CD4+ T cells, cells are stimulated with PMA (50 ng/mL) and ionomycin (500 ng/mL) for 4 hours in the presence of Brefeldin A (10 μg/mL), and then stained with peridinin-chlorophyll-protein (PerCP)-cy5.5-conjugated anti-CD4, PE-conjugated anti-Vβ8.1/8.2 and FITC-conjugated anti-CD8 antibodies (BD Biosciences).

For the intracellular markers, cells are subsequently fixed with 2% formaldehyde, permeabilized with 0.2% saponin and stained with PE-cy7-conjugated anti-IFNγ, APC-conjugated anti-IL-10 or APC-conjugated anti-IL-17 antibody (eBiosciences). Samples are read using a Beckman Coulter CyAn ADP and data are analyzed using Summit V4.3 (Dako). Cell sorting (>98% purity) is performed using a Beckman Coulter MoFlo XDP sorter.

Tissue Sample Preparation for Histological Analyses.

Pancreata are frozen in tissue freezing medium (Triangle Biomedical Sciences) and non-serial 8-μm thick sections are cut 150-μm apart. The sections are fixed in 4% formaldehyde for 10 minutes before histological procedures. For detection of eGFP expression in tissues, pancreata are fixed in 4% formaldehyde for 4 hours at 4° C. and immersed in 30% sucrose overnight before freezing. H&E staining is then performed to analyze insulitis.

Immunohistochemisty

For detection of β-cells, pancreatic sections are incubated with HRP-conjugated anti-insulin affibody molecule (Abcam) and the insulin+ cells are identified by incubating the slides with DAB chromogen and substrate (ScyTek) for 5 minutes. The nuclei are counterstained with hematoxylin.

Immunofluorescence

Pancreatic sections are treated with a PBS solution containing 1% BSA, 10% goat or donkey serum, and 0.2% Triton X-100. The sections are then incubated overnight at 4° C. in primary antibody (rabbit anti-insulin (Santa Cruz), guinea pig anti-insulin (Abcam), rabbit anti-PECAM1 (Santa Cruz), rabbit anti-Ki67 (Abcam), goat anti-VEGF (Santa Cruz). Slides are washed three times with Triton X-100 in PBS and then stained for 1 hour at room temperature with corresponding secondary antibody (Texas red-conjugated goat anti-rabbit IgG, FITC-conjugated goat anti-guinea pig IgG, FITC-conjugated donkey anti-goat IgG; Santa Cruz); DyLight 405-conjugated donkey anti-rabbit IgG or DyLight 549-conjugated donkey anti-goat IgG (Jackson ImmunoResearch). In some experiments, the cell nuclei are counterstained with DAPI (Santa Cruz).

Laser Capture Microdissection

Pancreatic sections are stained for insulin or PECAM1 and thoroughly dehydrated with Arcturus dehydration component. The insulin+ or PECAM1+ cells are dissected with CapSure HS LCM caps and the Autopix 100 laser capture microdissection system by following the manufacturer's instructions. For each individual mouse, cells are dissected from 3-10 non-serial sections. Genomic DNA is extracted from the dissected cells using the PicoPure DNA extraction kit (Applied Biosystems).

Detection of Y Chromosome by PCR.

Detection of Y chromosome and beta-actin is performed using 20 ng DNA template and Maxima qPCR master mix (Fermentas).

Quantitative PCR Analysis

Total RNA is extracted from pancreatic islets using the TRI RNA isolation reagent (Sigma). Quantitative PCR is performed using the Power SYBR Green kit and the StepOnePlus instrument (Applied Biosciences). The relative quantity (RQ) is calculated based on the ΔΔCT after normalization with the internal control 18S ribsome RNA expression.

It should be understood that various changes and modifications to the presently preferred embodiments described herein will be apparent to those skilled in the art. Such changes and modifications can be made without departing from the spirit and scope of the disclosed methods and without diminishing its intended advantages. It is therefore intended that such changes and modifications be covered by the appended claims.

Example 2

Ig-GAD2 Driven Immune Modulation is Not Sufficient to Overcome Overt Type I Diabetes An antigen specific therapy was tested in subjects with overt T1D. In an exemplary method, the GAD2 nucleotide sequence was inserted into the CDR3 variable region of the 91A3 heavy chain by PCR mutagenesis and the resulting chimeric heavy chain genes were analyzed by DNA sequencing. (See Example 1).

Surprisingly, while the Ig-GAD2 treatment restored normoglycemia in all of the hyperglycemic mice, none of the overt diabetic animals recovered from diabetes (FIG. 1A). More intriguing, the sick animals displayed eradication of Th17 cells and retention of Th1 cells in the spleen (FIG. 1B-D), similar to the immune modulation previously observed in the treatment of hyperglycemic mice (Jain et al., *J. Exp. Med.* 205:207-218 (2008)). In fact, the Ig-GAD2-treated diabetic mice had increased frequency of CD4$^+$CD8$^-$Vβ8.1/8.2+ T cells producing IFNγ and/or IL-10 (FIG. 1B), but diminished Th17 cells in the spleen or pancreas relative to untreated sick animals (FIG. 10). Moreover, there were reduced Th1 or Th17 cells in the pancreas because the mRNA for their signature transcription factors, T-bet and RORγt respectively, were significantly diminished (FIG. 1D). Overall, Ig-GAD2-driven immune modulation is not sufficient to restore normoglycemia in overtly diabetic mice.

Example 3

Transfer of BM Cells Alongside Ig-GAD2 Treatment Overcomes Overt T1D

Figure 2B:
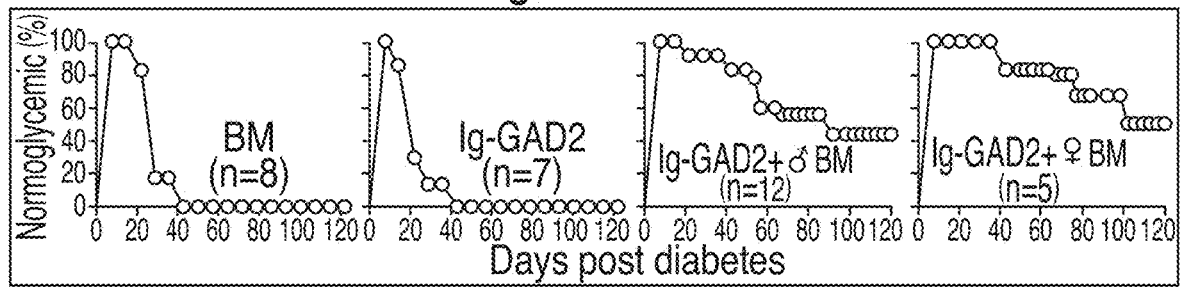
Figure 2C:
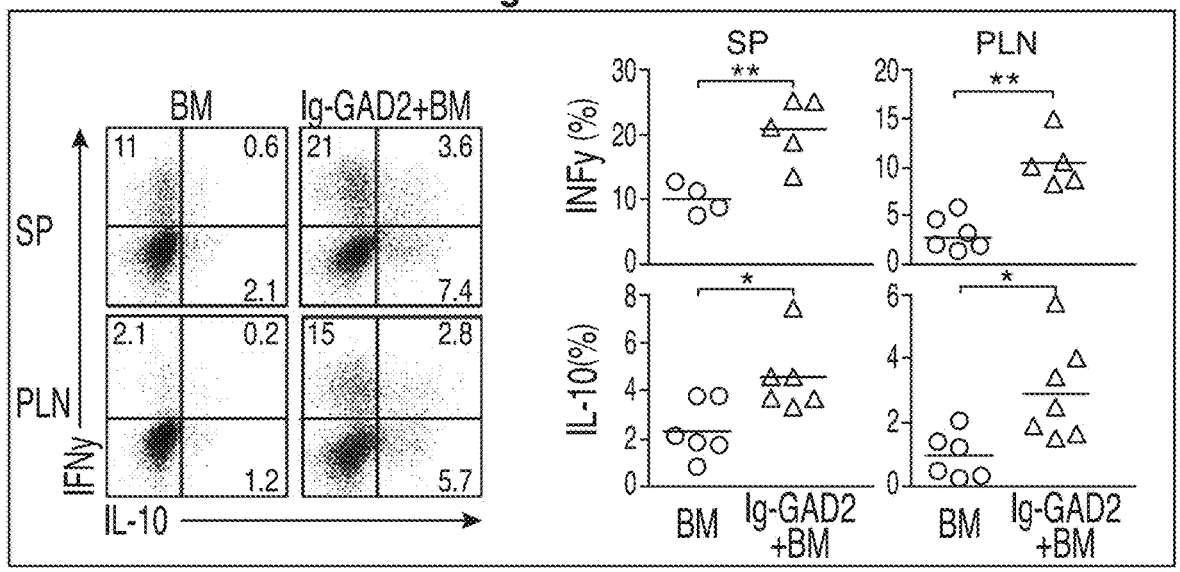
Figure 2D:
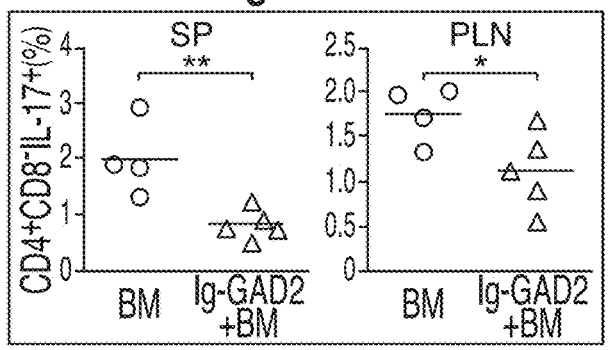
Figure 2E:
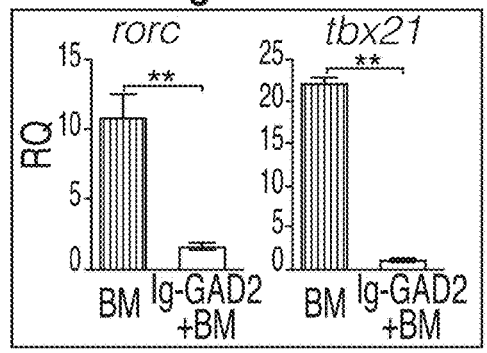
Figure 8:
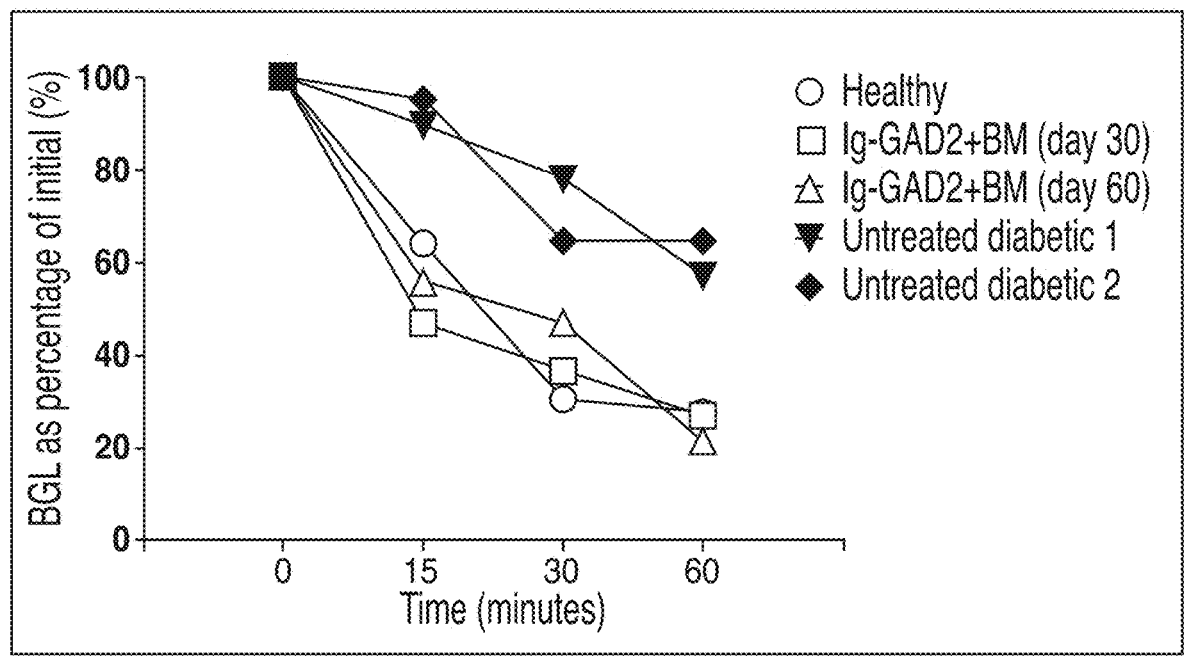
FIG. 8 shows that treatment of diabetic mice with Ig-GAD2+BM results in ablation of insulin-resistance associated with the onset of diabetes.

Bone marrow (BM) transplantations were performed to investigate whether concurrent treatment with the Ig-GAD2 and cell replacement therapy results in sustained recovery from overt diabetes. Accordingly, BM cell transfer from healthy donors was combined with a 70-day Ig-GAD2 treatment and assessed for restoration of normoglycemia (Treatment schematic shown in FIG. 2A). The majority of the mice given both Ig-GAD2 and BM transfer (Ig-GAD2+BM) were protected against disease regardless of whether the BM was from male or female donors, while no protection was observed in mice given Ig-GAD2 or BM alone (FIG. 2B). Treatment ablated insulin-resistance associated with the onset of diabetes (FIG. 8). Diabetic mice treated with the Ig-GAD2+BM regimen, like those recipient of Ig-GAD2 alone, had increased frequency of CD4$^+$CD8$^-$Vβ8.1/8.2+ T cells producing IFNγ and/or IL-10 (FIG. 2C), but diminished Th17 cells in the spleen and pancreas (FIG. 2D). In contrast, diabetic mice recipient of BM alone remained sick and had no increase in IFNγ and/or IL-10-producing cells or decrease in Th17 cells (FIG. 2C-D). Moreover, in the pancreas of Ig-GAD2+BM groups the mRNA for T-bet and RORγt was significantly diminished relative to animals recipient of BM alone (FIG. 2E) indicating that both Th1 and Th17 cells were minimal in this site. Thus, addition of BM transfer to the Ig-GAD2 regimen sustained recovery from diabetes without impacting immune modulation.

Example 4

BM Transfer Synergizes with Ig-GAD2 to Drive Formation of Healthy Islets

Figure 3A:
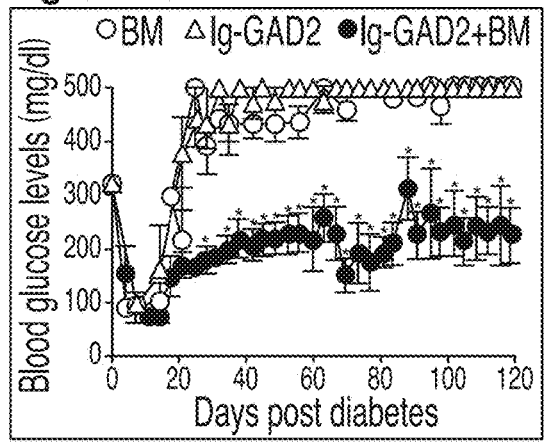
FIG. 3A-G shows regeneration of pancreatic β-cells in Ig-GAD2+BM recipient mice.
Figure 3B:
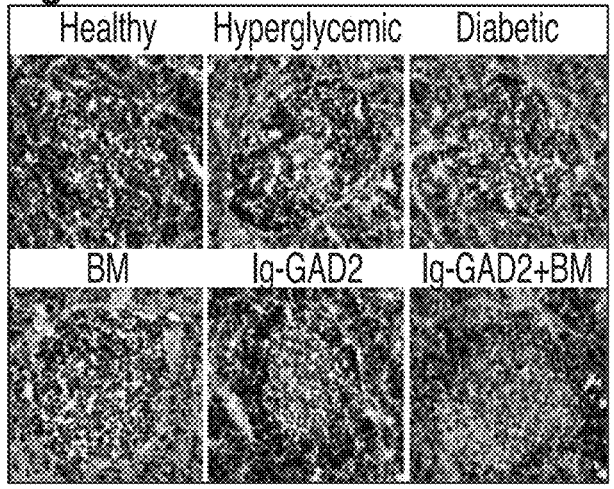
Figure 3C:
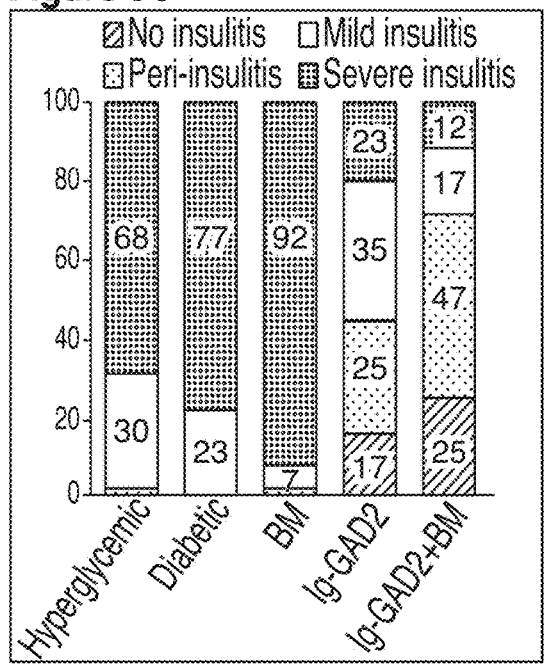
Figure 3D:
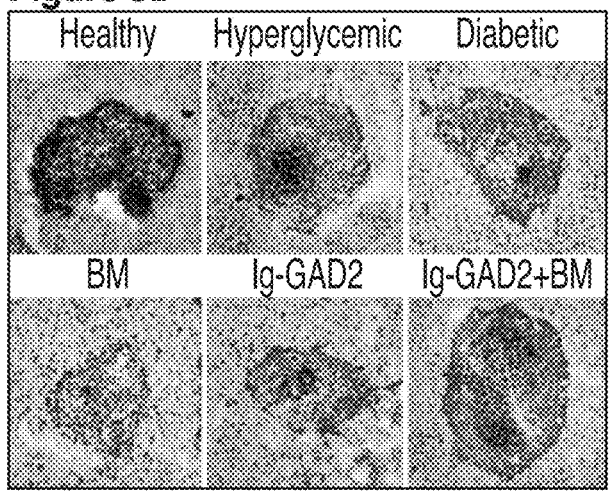
Figure 3E:
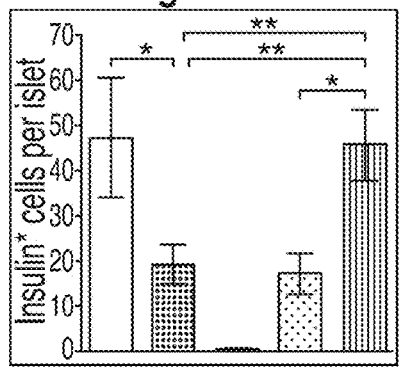
Figure 3F:
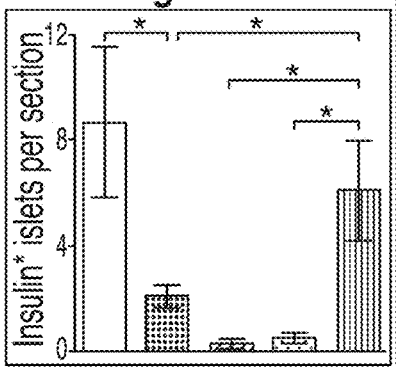
Figure 3G:
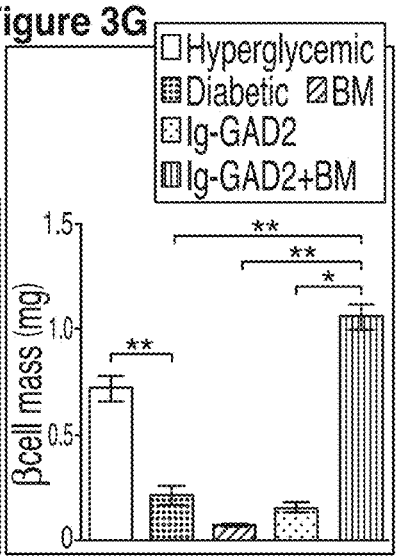

Since Ig-GAD2+BM but not Ig-GAD2 alone restored normoglycemia, it is likely that addition of BM transfer sustained regeneration of β-cells that were able to thrive under minimal inflammation curtailed by Ig-GAD2. To test these premises, the mice treated with Ig-GAD2+BM which displayed consistent return to normoglycemia compared to those recipient of Ig-GAD2 of BM alone (FIG. 3A) were examined for reduction in pancreatic infiltration and formation of healthy islet. Mice recipient of the Ig-GAD2+BM treatment had islets that were mostly free of insulitis or islets that had minimal infiltration in the form of peri-insulitis (FIG. 3B-C). The mice recipient of Ig-GAD2 alone, which were unable to recover from diabetes, had islets with no peri-insulitis indicative of effective immune modulation. In contrast, the animals recipient of BM alone had mostly severe insulitis (FIG. 3B-C). Moreover, while the mice treated with Ig-GAD2+BM had structured islets with abundant insulin-positive cells those given Ig-GAD2 or BM alone had less islets with fewer β-cells like untreated, recently diagnosed diabetic mice (FIG. 3D). Compiled results indicate a significant increase in the number of insulin-producing β-cells, the number of islets and the mass of β-cells in Ig-GAD2+BM-treated mice that were not evident in animals recipient of Ig-GAD2 or BM alone (FIG. 3E-G). Thus, the enrichment with BM cells synergized with Ig-GAD2-driven immune modulation to sustain an increase in the number of β-cells that were able to thrive and maintain normoglycemia.

Example 5

Figure 9:
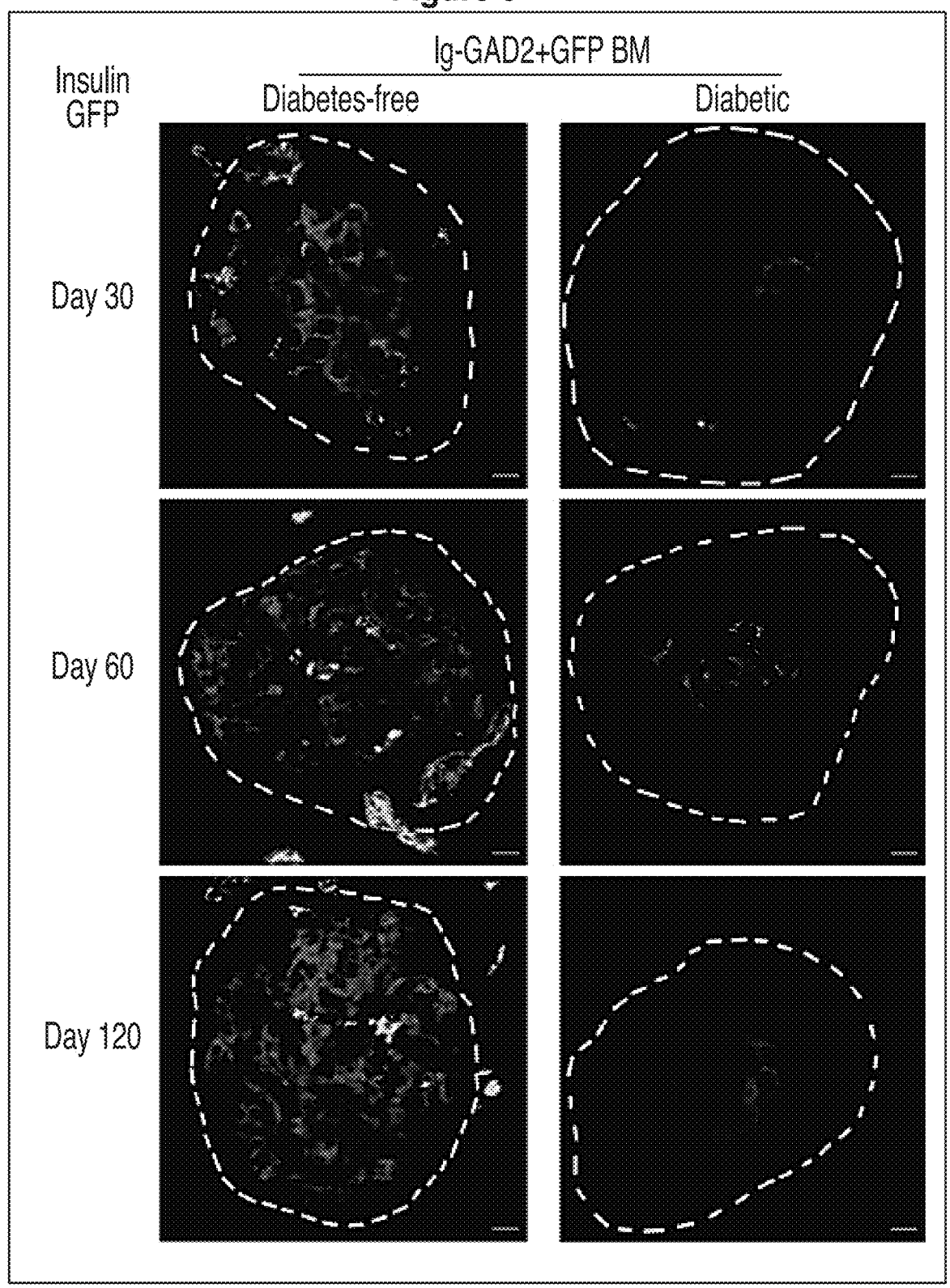
FIG. 9 shows no colocalization of donor BM-derived cells and insulin producing cells at 30-, 60- or 120-days during Ig-GAD2+BM treatment (left panels). Donor BM-derived cells were abundant in the diabetes-free mice, but minimal in those recipients of the same regimen that remained diabetic (right panels).

Mice Recipient of BM Transfer and Ig-GAD2 Treatment Display Increased Endothelial Cell Numbers in the Pancreatic Islets To determine the origin of the newly formed β-cells in the mice treated with Ig-GAD2+BM NOD-GFP mice were used as a source of BM and insulin-producing β-cells were assessed for GFP expression following treatment. The results show that there was no GFP/insulin colocalization at any time point during Ig-GAD2+BM treatment (FIG. 9). Furthermore, the GFP+ cells, which were abundant in the diabetes-free mice, were minimal in those recipient of the same regimen but remained diabetic (FIG. 9). Thus, the BM transfer did not appear to serve as a source of insulin-producing β-cells but rather yielded engraftment of GFP+ cells in the islets of the recovering mice. Therefore, the β-cells surprisingly did not originate from the donor cells as was observed in other models (Hess et al., *Nat. Biotechnol.,* 21:763-770 (2003); Mathews et al., *Diabetes,* 53:91-98 (2004); Choi et al., *Diabetologia,* 105:16242-16247 (2003); Lechner et al., *Diabetes,* 53:616-623 (2004)).

The next question was whether the GFP+ engraftment represents cells that could not be provided by the host's BM but are required for maintenance of endogenous β-cells. The results showing a significant decrease in the frequency of both circulating and intra-islet PECAM1+ ECs in diabetic versus healthy mice (FIG. 4). Indeed, there was a dramatic decrease in the frequency of peripheral blood ECs as the mice progressed towards overt diabetes (FIG. 4A-B). Similarly, the frequency of ECs in the pancreatic islets diminished as the mice became diabetic, a phenomenon that correlates with the loss of β-cells (FIG. 4C-D). This indicates that the frequency of ECs is diminished both in the peripheral blood and the pancreas in diabetic mice.

Figure 5B:
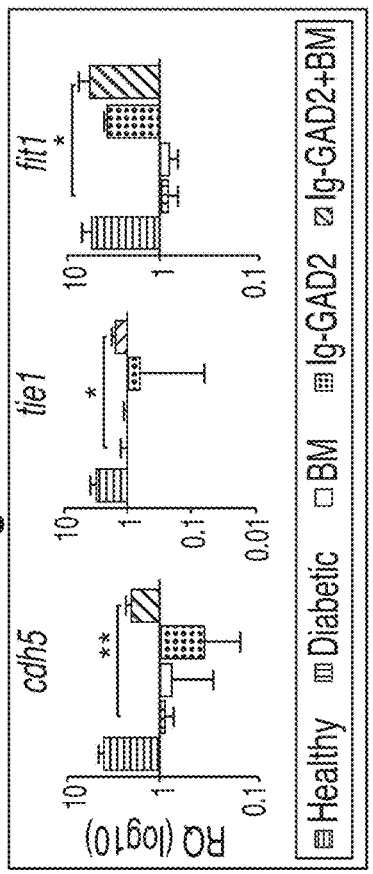
FIG. 5A-C shows that restoration of the endothelial cells parallels with β-cell regeneration.
Figure 5C:
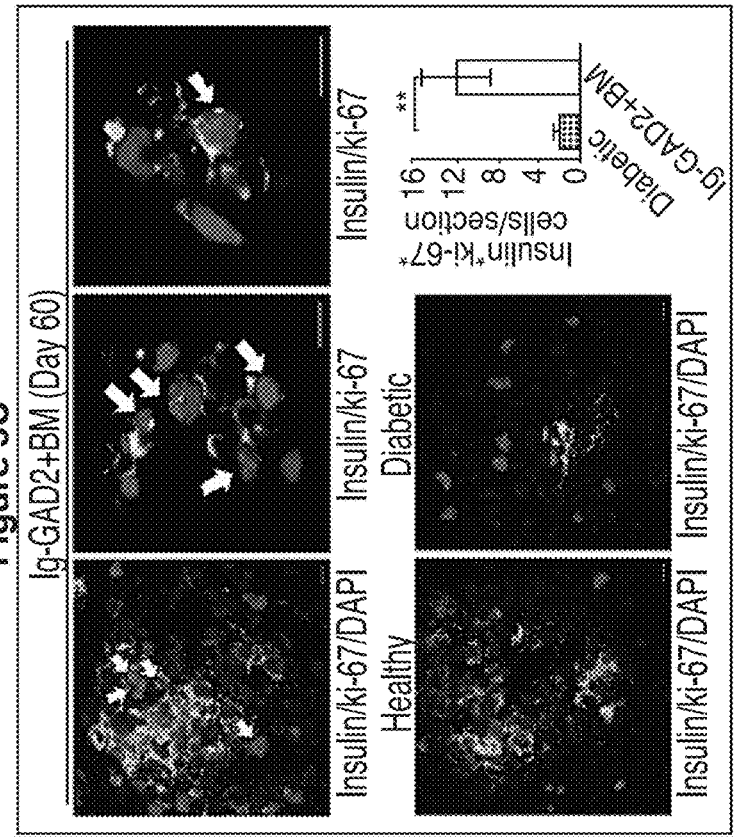
Figure 5A:
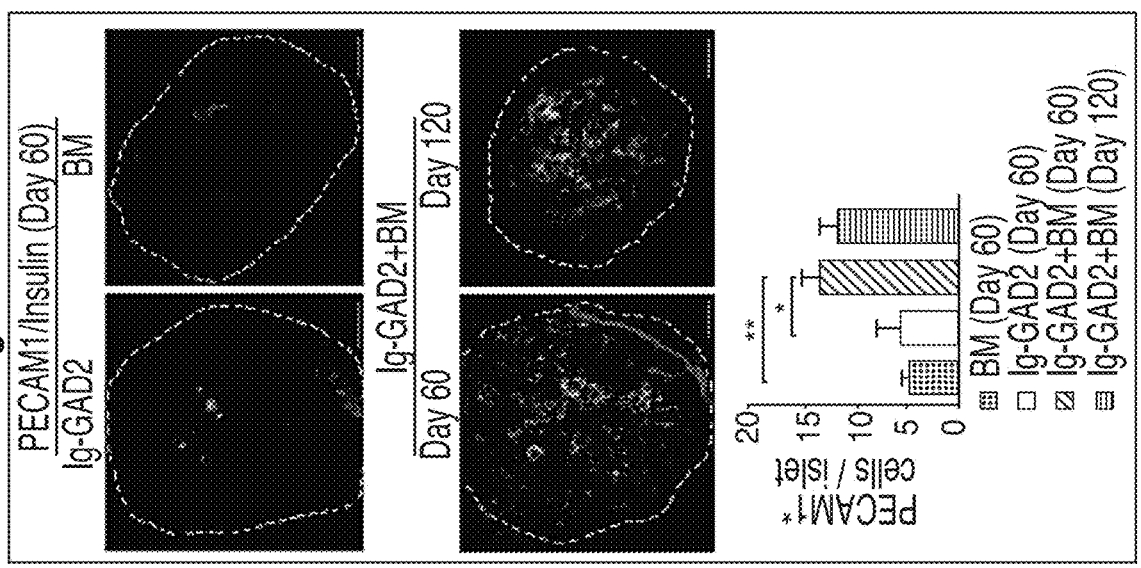
Figure 10A:
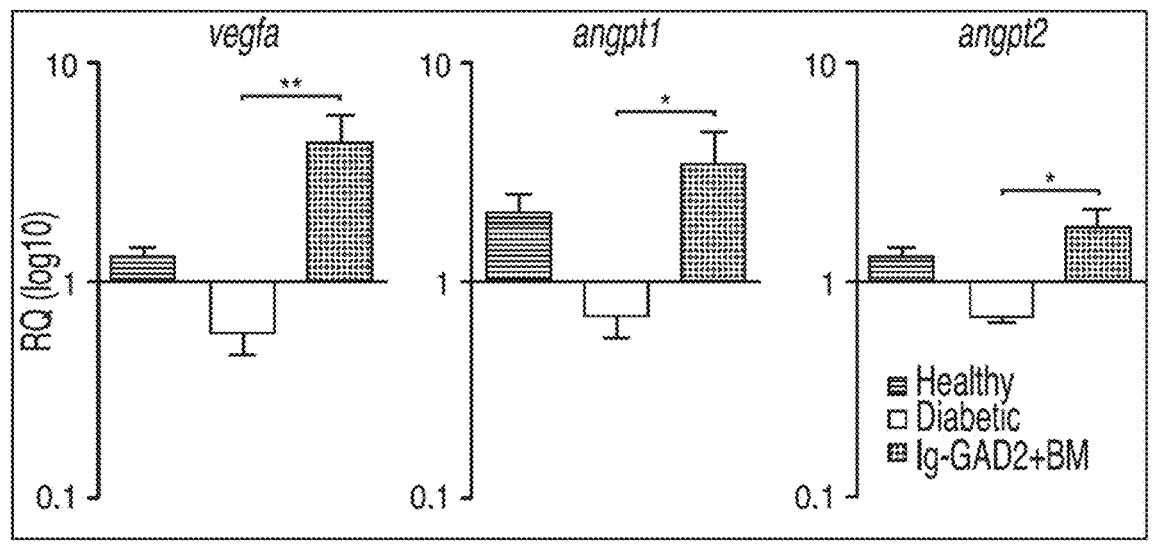
FIG. 10A-B shows up-regulation of genes encoding angiogenic factors, including VEGFa, angiopoietin 1 and angiopoeitin 2 in the pancreas of diabetes-free mice treated with IgGAD2+BM (FIG. 10A).
Figure 10B:
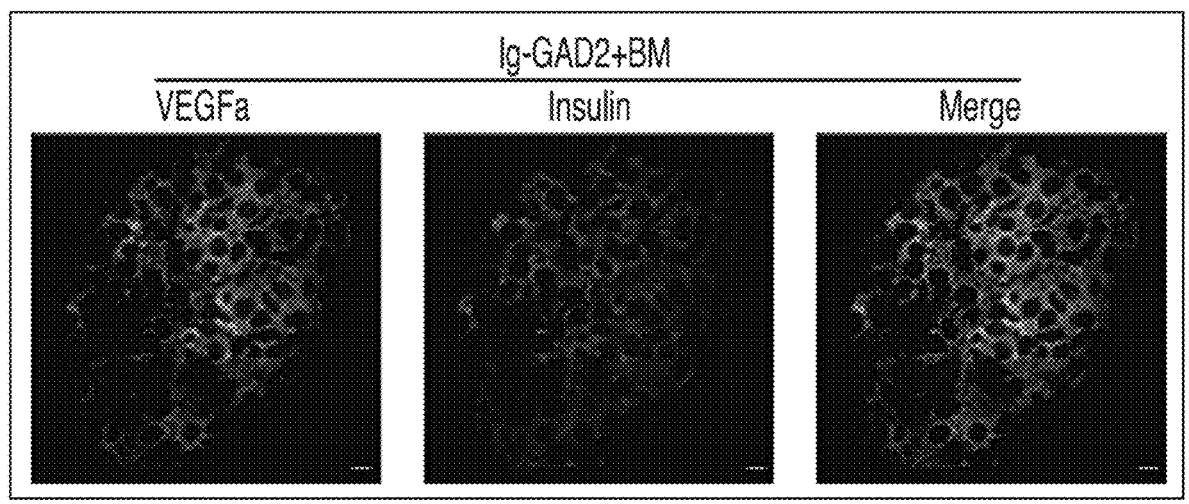

Interestingly, the mice recipient of Ig-GAD2+BM but not those given Ig-GAD2 or BM alone restored the PECAM1+ endothelial cells (ECs) in the islets (FIG. 5A). Moreover, when the expression of genes encoding VE-cadherin (Cdh5), angiopoietin receptor (Tie1) and VEGF receptor 1 (Flt1) which represent functional markers for ECs were analyzed, there was a significant mRNA increase for these genes in the mice recipient of Ig-GAD2+BM relative to untreated diabetic animals (FIG. 5B). Those given Ig-GAD2 or BM alone did not display a similar increase in the expression of the genes (FIG. 5B). The increase in ECs likely fosters angiogenesis for better islet vascularization and thriving of β-cells. In fact, there was a strong up-regulation of genes encoding angiogenic factors, including VEGFa (vegfa), angiopoietin 1 (angpt1), and angiopoietin 2 (angpt2) in the pancreas of diabetes-free mice treated with Ig-GAD2+BM (FIG. 10A). Furthermore, the newly-formed β-cells produced VEGFa (FIG. 10B), which is critical for development of endothelial cells and islet vascularization (Brissova et al., *Diabetes*, 55:2974-2985 (2006); Lammert et al., *Curr. Biol.*, 13:1070-1074 (2003)). The symbiotic relationship among endothelial and β cells is further evidenced by the parallel restoration of β-cell division in the Ig-GAD2+BM cell transfer mice (FIG. 5C). Indeed, the β-cells displayed significant staining for the proliferation marker ki-67 when compared to resting β-cells in normal mice or to residual β-cells in untreated diabetic mice (FIG. 5C). These results suggest that BM transfer during treatment with Ig-GAD2 sustained repair of the endothelial network leading to efficient regeneration of β-cells. The latter were able to produce the vital angiogenic factor VEGFa to maintain symbiosis and the health of the islets.

Example 6

Donor BM Transfer Gives Rise to Islet Endothelial Cells

To test whether the engrafted donor BM derived GFP+ cells represent ECs we examined the GFP+ cells for expression of the endothelial marker PECAM1 and for localization relative to insulin-producing β cells. The results show that in the diabetes-free mice there were GFP+ cells in the islets that expressed PECAM1 as indicated by the colocalization of the two markers at both day 30 and 60 of treatment (FIG. 6A). Such colocalization was not observed in mice recipient of the same regimen that remained diabetic. Also, the GFP+PECAM1+ cells did not colocalize with insulin staining, indicating that the BM transfer gives rise to ECs during protection against T1D. These observations are supported by the detection of Y chromosome in the endothelial but not in β-cells when the BM transfer was from male donors. Indeed, Y chromosome was detectable when the DNA was extracted from bulk pancreatic cells in mice recipient of Ig-GAD2+BM (FIG. 6B). More specifically, when PECAM1+ and insulin+ cells were micro-dissected using a laser-capture system and their genomic DNA was analyzed by PCR, the Y chromosome was detected in PECAM1+ but not insulin+ cells and this was restricted to diabetes-free mice given Ig-GAD2+BM transfer (FIG. 6C-D). These results indicate that donor BM gives rise to ECs that are required for recovery from diabetes.

Example 7

Figure 7A:
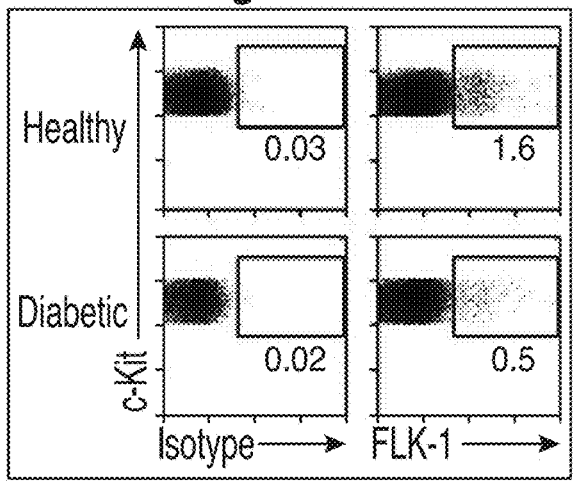
FIG. 7A-D shows that transfer of endothelial cell progenitors during treatment with Ig-GAD2 sustains β-cell regeneration and restores normoglycemia.
Figure 7B:
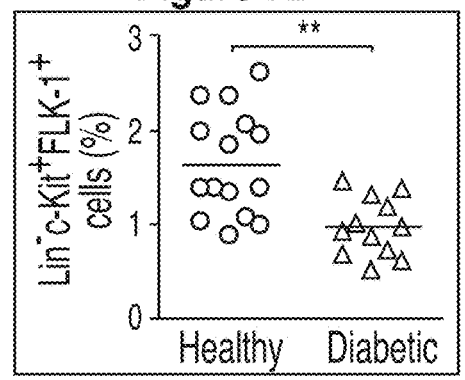

Endothelial Progenitor Cells Substitute for BM Transfer and Assist Ig-GAD2 for Reversal of T1D To test whether transfer of donor EPCs alongside Ig-GAD2 treatment would yield mature ECs capable of assisting the survival and function of β cells and restoration of normoglycemia EPCs were purified from BM of healthy NOD-GFP mice and substituted for whole BM. Notably, the BM lineage-negative (Lin$^-$) population expressing the EPC markers c-Kit and FLK-1 was significantly reduced in the diabetic versus age-matched healthy mice (FIG. 7A-B).

Figure 7C:
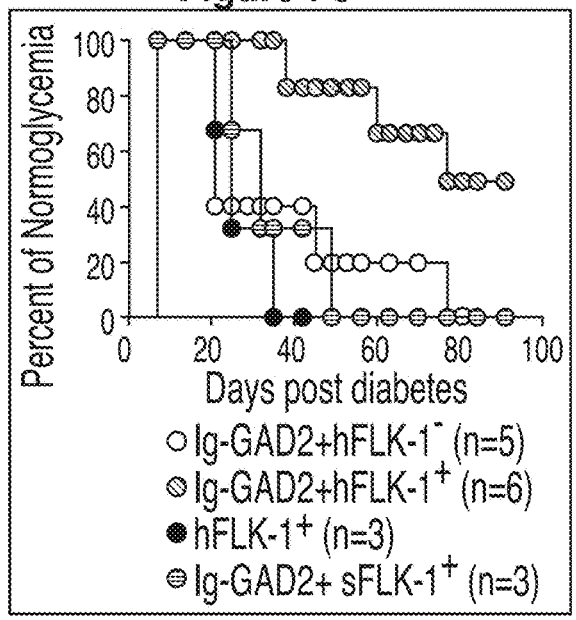
Figure 7D:
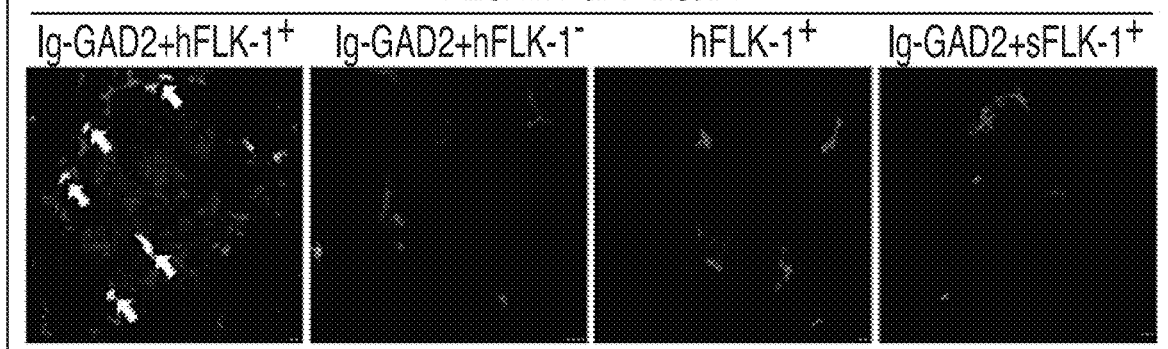

Transfer of purified GFP$^+$Lin$^-$c-Kit$^+$FLK-1$^+$ (hFLK-1$^+$) cells from healthy donors, replacing whole BM transfer during treatment with Ig-GAD2, resulted in most of the mice recovering from the disease while the control group given Lin$^-$c-Kit$^+$FLK-1$^-$ (hFLK-1$^-$) cells had a much lower recovery rate despite receiving a 60-times higher cell number (FIG. 7C). In addition, no significant recovery from disease was observed when the hFLK-1$^+$ cells were transferred without Ig-GAD2 (FIG. 7C). When the FLK-1$^+$ cells were derived from sick NOD-GFP mice (sFLK-1$^+$), there was minimal recovery of the disease (FIG. 7C). Furthermore, there was no evident GFP+ cells in the islets of these mice which explains the lack of increase in PECAM1$^+$ cells (compare right to left panel in FIG. 7D). In fact, similar results were observed in the mice that did not recover from diabetes under the Ig-GAD2+FLK-1$^-$ or FLK-1$^+$ cells without Ig-GAD2 (FIG. 7D). These results indicate that EPCs can substitute for BM transfer and give rise to mature ECs that help β-cells thrive and restore normoglycemia. Furthermore, maturation of the EPCs and increase in ECs occurs only when EPCs originate from healthy donors, which explains the inability of diabetic mice to utilize their own EPCs for repair of the pancreatic endothelial network.

Example 8

Treatment of Subject with Type 1 Diabetes

Studies are conducted to determine the effects of a composition comprising an amount of one or more stem and/or progenitor cells and an amount of at least one antigen-specific therapy in subjects with T1D. For example, a multicenter, randomized, double-blind, placebo-controlled study is undertaken to evaluate treatment with a weight-based or fixed dose of a composition comprising an amount of one or more stem and/or progenitor cells and an amount of at least one antigen-specific therapy in human subjects diagnosed with T1D. More specifically, a clinical study was performed to examine the efficacy and safety of a composition comprising an amount of one or more stem and/or progenitor cells and an amount of at least one antigen-specific therapy. The composition is effective to treat including, prevent, T1D.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein can be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the disclosure so claimed are inherently or expressly described and enabled herein.

It is to be understood that the embodiments of the disclosure disclosed herein are illustrative of the principles of the present disclosure. Other modifications that can be employed are within the scope of the disclosure. Thus, by way of example, but not of limitation, alternative configurations of the present disclosure can be utilized in accordance with the teachings herein. Accordingly, the present disclosure is not limited to that precisely as shown and described.

While the present disclosure has been described and illustrated herein by references to various specific materials, procedures and examples, it is understood that the disclosure is not restricted to the particular combinations of materials and procedures selected for that purpose. Numerous variations of such details can be implied as will be appreciated by those skilled in the art. It is intended that the specification and examples be considered as exemplary, only, with the true scope and spirit of the disclosure being indicated by the following claims. All references, patents, and patent applications referred to in this application are herein incorporated by reference in their entirety.

The invention claimed is:

1. A composition comprising an amount of purified autologous endothelial progenitor cells and an amount of at least one immunoglobulin-polypeptide chimera, wherein the immunoglobulin-peptide chimera expresses a disease-specific T- or B-cell epitope.

2. The composition of claim 1, wherein the purified endothelial progenitor cells are isolated from bone marrow.

3. The composition of claim 1, wherein the purified endothelial progenitor cells are purified bone marrow endothelial progenitor cells.

4. The composition of claim 1, wherein the immunoglobulin-polypeptide chimera is soluble.

5. The composition of claim 1, wherein the immunoglobulin-polypeptide chimera is aggregated.

6. The composition of claim 1, wherein the immunoglobulin-polypeptide chimera comprises an immunoglobulin having a CDR3 region, and wherein a diabetogenic epitope is inserted within the CDR3 region.

7. The composition of claim 6, wherein the diabetogenic epitope comprises GAD2 (SEQ ID NO: 1), GAD1 (SEQ ID NO: 2) or INSβ (SEQ ID NO: 3).

8. The composition of claim 1 comprising no other cell types other than purified endothelial cells.

9. A composition comprising:
    an amount of cells, wherein the cells consist essentially of purified autologous endothelial progenitor cells; and
    an amount of at least one immunoglobulin-polypeptide chimera, wherein the immunoglobulin-peptide chimera expresses a disease-specific T- or B-cell epitope.

10. The composition of claim 9, wherein the immunoglobulin-polypeptide chimera comprises an immunoglobulin having a CDR3 region, and wherein a diabetogenic epitope is inserted within the CDR3 region.

11. The composition of claim 10, wherein the diabetogenic epitope comprises GAD2 (SEQ ID NO: 1), GAD1 (SEQ ID NO: 2) or INSβ (SEQ ID NO: 3).

12. The composition of claim 1, wherein the composition comprises no or substantially no cells that are $Lin^+$, $c\text{-}Kit^-$, and/or $FLK\text{-}1^-$.

13. The composition of claim 9, wherein the composition comprises no or substantially no cells that are $Lin^{31}$, $c\text{-}Kit^-$, and/or $FLK\text{-}1^-$.

* * * * *

SEQUENCE LISTING

<160> NUMBER OF SEQ ID NOS: 23

<210> SEQ ID NO 1
<211> LENGTH: 15
<212> TYPE: PRT
<213> ORGANISM: Mus musculus

<400> SEQUENCE: 1

Thr Tyr Glu Ile Ala Pro Val Phe Val Leu Leu Glu Tyr Val Thr
1               5                   10                  15

<210> SEQ ID NO 2
<211> LENGTH: 20
<212> TYPE: PRT
<213> ORGANISM: Mus musculus

```
<400> SEQUENCE: 2

Ser Arg Leu Ser Lys Val Ala Pro Val Ile Lys Ala Arg Met Met Glu
1               5                   10                  15

Tyr Gly Thr Thr
            20

<210> SEQ ID NO 3
<211> LENGTH: 15
<212> TYPE: PRT
<213> ORGANISM: Mus musculus

<400> SEQUENCE: 3

Ser His Leu Val Glu Ala Leu Tyr Leu Val Cys Gly Glu Arg Gly
1               5                   10                  15

<210> SEQ ID NO 4
<211> LENGTH: 19
<212> TYPE: DNA
<213> ORGANISM: Mus musculus

<400> SEQUENCE: 4
ggtgagaggc acaagttgg                                                19

<210> SEQ ID NO 5
<211> LENGTH: 20
<212> TYPE: DNA
<213> ORGANISM: Mus musculus

<400> SEQUENCE: 5
atctctgtgc ctcctggaaa                                               20

<210> SEQ ID NO 6
<211> LENGTH: 24
<212> TYPE: DNA
<213> ORGANISM: Mus musculus

<400> SEQUENCE: 6
gcttctttgc agctccttcg ttgc                                          24

<210> SEQ ID NO 7
<211> LENGTH: 24
<212> TYPE: DNA
<213> ORGANISM: Mus musculus

<400> SEQUENCE: 7
gtgtccgttc tgagtgatcc tcag                                          24

<210> SEQ ID NO 8
<211> LENGTH: 22
<212> TYPE: DNA
<213> ORGANISM: Mus musculus

<400> SEQUENCE: 8
agcatctgga gcatgtgatg ga                                            22

<210> SEQ ID NO 9
<211> LENGTH: 21
<212> TYPE: DNA
<213> ORGANISM: Mus musculus

<400> SEQUENCE: 9
tatctcaagc atggtggccg t                                             21
```

```
<210> SEQ ID NO 10
<211> LENGTH: 22
<212> TYPE: DNA
<213> ORGANISM: Mus musculus

<400> SEQUENCE: 10
aacaccgaga agatggcagt gt                                              22

<210> SEQ ID NO 11
<211> LENGTH: 22
<212> TYPE: DNA
<213> ORGANISM: Mus musculus

<400> SEQUENCE: 11
agacaaactc attgcccagc ca                                              22

<210> SEQ ID NO 12
<211> LENGTH: 22
<212> TYPE: DNA
<213> ORGANISM: Mus musculus

<400> SEQUENCE: 12
ttcgcaccag gtattcaacg ca                                              22

<210> SEQ ID NO 13
<211> LENGTH: 22
<212> TYPE: DNA
<213> ORGANISM: Mus musculus

<400> SEQUENCE: 13
tcatctgcat ccactgctgt ca                                              22

<210> SEQ ID NO 14
<211> LENGTH: 21
<212> TYPE: DNA
<213> ORGANISM: Mus musculus

<400> SEQUENCE: 14
tgcaggaaac cacagcagga a                                               21

<210> SEQ ID NO 15
<211> LENGTH: 22
<212> TYPE: DNA
<213> ORGANISM: Mus musculus

<400> SEQUENCE: 15
ttcaatgttg caggcgagcc at                                              22

<210> SEQ ID NO 16
<211> LENGTH: 22
<212> TYPE: DNA
<213> ORGANISM: Mus musculus

<400> SEQUENCE: 16
cagcatgaaa cttcgcaagc ca                                              22

<210> SEQ ID NO 17
<211> LENGTH: 22
<212> TYPE: DNA
<213> ORGANISM: Mus musculus

<400> SEQUENCE: 17
tgggcacttc aaactctgct gt                                              22
```

```
<210> SEQ ID NO 18
<211> LENGTH: 22
<212> TYPE: DNA
<213> ORGANISM: Mus musculus

<400> SEQUENCE: 18
tgcaggctgc tgtaacgatg aa                                              22

<210> SEQ ID NO 19
<211> LENGTH: 22
<212> TYPE: DNA
<213> ORGANISM: Mus musculus

<400> SEQUENCE: 19
tgctgtgctg taggaagctc at                                              22

<210> SEQ ID NO 20
<211> LENGTH: 22
<212> TYPE: DNA
<213> ORGANISM: Mus musculus

<400> SEQUENCE: 20
tccaagttca accagcacca ga                                              22

<210> SEQ ID NO 21
<211> LENGTH: 22
<212> TYPE: DNA
<213> ORGANISM: Mus musculus

<400> SEQUENCE: 21
tccaccaaga ccacatccac aa                                              22

<210> SEQ ID NO 22
<211> LENGTH: 22
<212> TYPE: DNA
<213> ORGANISM: Mus musculus

<400> SEQUENCE: 22
acagccactg cattcccagt tt                                              22

<210> SEQ ID NO 23
<211> LENGTH: 22
<212> TYPE: DNA
<213> ORGANISM: Mus musculus

<400> SEQUENCE: 23
tctcggaagg acttgcagac at                                              22
```